United States Patent
Ephraim et al.

(10) Patent No.: US 11,559,065 B2
(45) Date of Patent: Jan. 24, 2023

(54) COMPOSITIONS AND METHODS OF TREATING AND REDUCING RISK OF CONDITIONS ASSOCIATED WITH ELEVATED 4-ETHYLPHENYL SULFATE IN CANINES AND IDENTIFYING CANINES AT RISK OF SUCH CONDITIONS

(71) Applicant: Hill's Pet Nutrition, Inc., Topeka, KS (US)

(72) Inventors: Eden Ephraim, Lawrence, KS (US);
Dennis Jewell, Lawrence, KS (US);
Jeffrey Brockman, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 400 days.

(21) Appl. No.: 16/721,444

(22) Filed: Dec. 19, 2019

(65) Prior Publication Data

US 2021/0186053 A1     Jun. 24, 2021

(51) Int. Cl.
| | | |
|---|---|---|
| C12Q 1/68 | (2018.01) | |
| C07H 21/04 | (2006.01) | |
| A23K 10/37 | (2016.01) | |
| C12Q 1/6827 | (2018.01) | |
| A23K 50/40 | (2016.01) | |
| A61K 36/81 | (2006.01) | |

(52) U.S. Cl.
CPC ............ *A23K 10/37* (2016.05); *A23K 50/40* (2016.05); *A61K 36/81* (2013.01); *C12Q 1/6827* (2013.01); *C12Q 2600/156* (2013.01)

(58) Field of Classification Search
None
See application file for complete search history.

(56) References Cited

FOREIGN PATENT DOCUMENTS

KR     102124652 B1     6/2020

OTHER PUBLICATIONS

Jonathan Massey (Thesis: Mapping the genes for complex canine autoimmune diseases; The university of Manchester 2012). (Year: 2012).*
Yuangklang et al. J of Applied Animal Welfare Science, "Digestibility of sundried tomato pomace in dogs", pp. 35-42, Oct. 2015. (Year: 2015).*
Vetnutrition Blogspot, "Factoid: Tomato pomace" http://vetnutrition.blogspot.com/2009/05/factoid-tomato-pomace.html; May 14, 2009. (Year: 2009).*

(Continued)

*Primary Examiner* — Jeanine A Goldberg

(57) ABSTRACT

Methods of identifying canine subjects having an increased likelihood of developing elevated levels of 4-ethylphenyl sulfate, canine stress, canine anxiety and/or an inhibition of growth of beneficial microbes and promotion of growth of harmful microbes are disclosed. Methods comprise analyzing a biological sample obtained from the canine subject for the presence of two copies of a minor allele of the single nucleotide polymorphism BICF2P1175095 in a canine subject. Methods of treating the identified canine subjects by administering an effective amount of tomato pomace are also disclosed. Methods of treating canine subjects for elevated 4-EPS levels, canine anxiety or canine stress are disclosed. Canine food compositions that comprises tomato pomace are disclosed.

12 Claims, 1 Drawing Sheet

Specification includes a Sequence Listing.

(56) References Cited

OTHER PUBLICATIONS

Dodman et al., 2009, "A canine chromosome 7 locus confers compulsive disorder susceptibility", Molecular Psychiatry, 15(1):8-10.
Gebreselassie et al., 2018, "Anti-aging Food that Imparts Health Benefits to Senior Dogs by Modulating the Gut Microbiome and Metabolites (P11-003)", Current Developments in Nutrition, 2(11):nzy038 (2 pages).
International Search Report and the Written Opinion of the International Searching Authority issued in International Application PCT/US2019/067567 dated Sep. 11, 2020, (12 pages).
Milgram et al., 2004, "Long-term treatment with antioxidants and a program of behavioral enrichment reduces age-dependent impairment in discrimination and reversal learning in beagle dogs", Experimental Gerontology, 39(5):753-765.
Van Rooy et al., 2016, "Evaluating candidate genes oprm1, drd2, avpr1a, and oxtr in golden retrievers with separation-related behaviors", Journal of Veterinary Behavior: Clinical Applications and Research, Elsevier, 16:22-27.
Vaysse et al., 2011, "Identification of Genomic Regions Associated with Phenotypic Variation between Dog Breeds using Selection Mapping", PLOS Genetics, 7(10):e1002316, (21 pages).
Zapata et al., 2016, "Genetic mapping of canine fear and aggression", BMC Genomics, 17(1):1-20.

\* cited by examiner

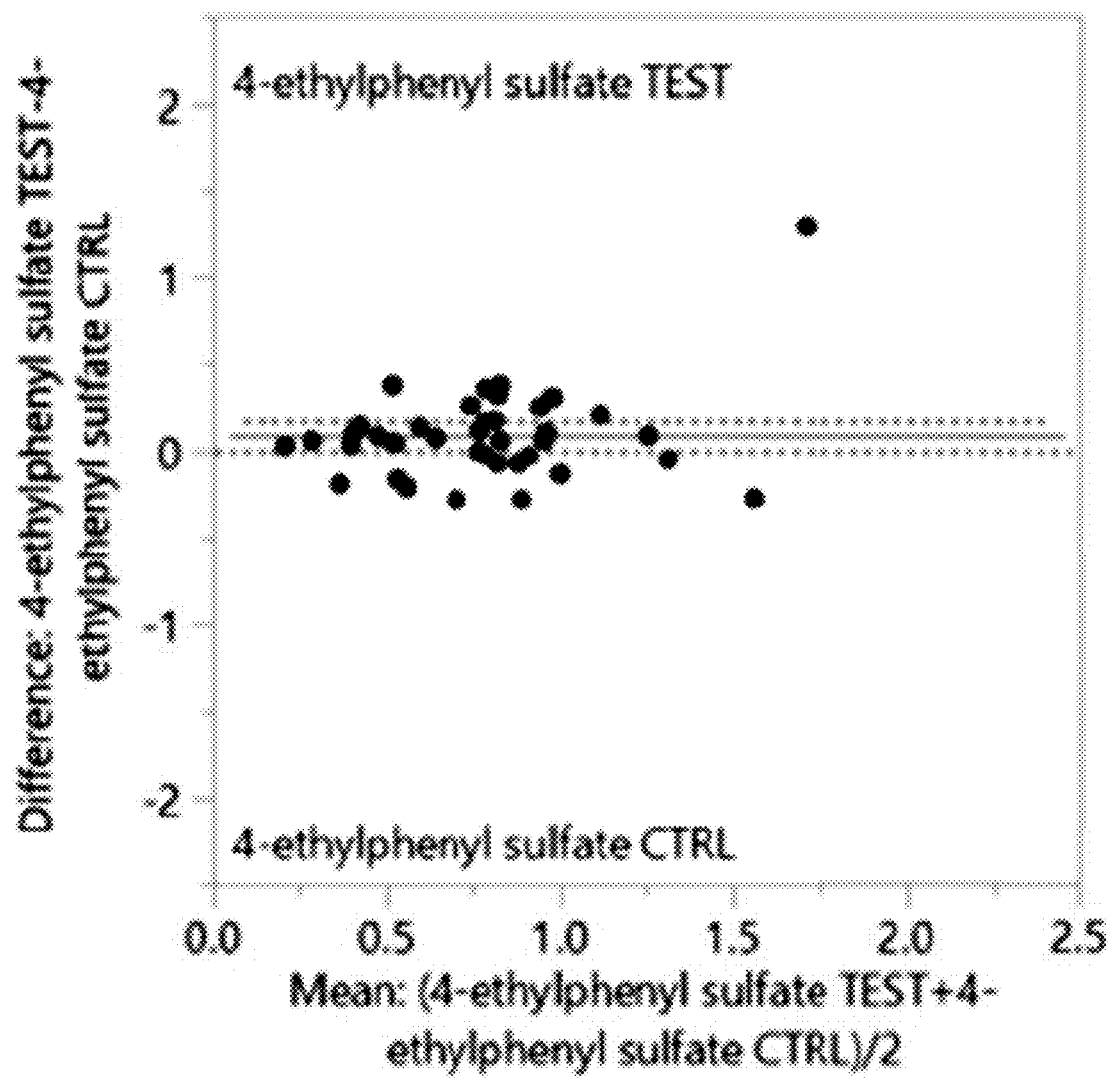

SEQUENCE LISTING

```
<160> NUMBER OF SEQ ID NOS: 1

<210> SEQ ID NO 1
<211> LENGTH: 201
<212> TYPE: DNA
<213> ORGANISM: Canis familiaris

<400> SEQUENCE: 1
tatttgtctt gaaatttcat tataagctta atttttcctt gttgttggta tcagactacc      60
gtgtatgctt gttttctgtt tccctccacg gcaatctacc raaataaaat gaggtgtggt     120
tcctttgtcc tttctgtaac tctcagtcct cccccccacc ccatatcctt tacttgagga    180
gggagactac atctaatttg g                                              201
```

COMPOSITIONS AND METHODS OF TREATING AND REDUCING RISK OF CONDITIONS ASSOCIATED WITH ELEVATED 4-ETHYLPHENYL SULFATE IN CANINES AND IDENTIFYING CANINES AT RISK OF SUCH CONDITIONS

BACKGROUND

The microbial toxin, 4-ethylphenyl sulfate (4-EPS) is a metabolite produced by gut microbes. Among other microbial metabolites, 4-EPS enters the systemic circulation. In canines, increased levels of 4-EPS in the blood is associated with stress, anxiety, brain damage and other behavioral issues. Reduction in levels of 4-EPS has been shown to alleviate symptoms of stress and anxiety.

Canine anxiety (anxiety) is a response to fear and agitation, or apprehension when the dog anticipates a threat or fearful situation. Some individual dogs experience disproportionate levels of anxiety. Anxiety can develop into an anxiety disorder and can lead to behavioral and other issues. Some dogs experience a generalized anxiety, in which the fearful reaction is displayed in a wide range of situations to which a "normal" pet would be unlikely to react. Anxiety can take the form of one of various anxiety disorders such as generalized anxiety disorders, excessive stimulus anxiety, separation anxiety, confinement, noise phobias, among others.

Causative factors may include genetic components, prenatal and neonatal stressors, maternal separation, lack of socialization, unfamiliarity, or a previous unpleasant outcome during encounters with the stimulus (or similar stimuli). The most common causes are fear, separation and aging. Fear-related anxiety can be caused by loud noises, strange people or animals, visual stimuli, new or strange environments, and specific situations among others. Age-related anxiety affects older dogs and can be associated with cognitive dysfunction syndrome (CDS). Separation anxiety is a specific anxiety arising from an inability of the pet to find comfort when separated from family members. About 14% of dogs have separation anxiety. Some separation anxiety may be the result of dysfunctional attachment as a puppy ages and matures. In some cases, separation anxiety may arise in cases involving a change in household or daily routine, while in others separation anxiety is associated with an underlying state of anxiety along with other behavioral issues such as phobias.

Anxiety may lead to destructive behavior (particularly at exits or toward owner possessions), distress vocalization, house-soiling, salivation, pacing, restlessness, inability to settle, anorexia, and repetitive or compulsive behaviors. In some instances, anxiety may play a role in aggressive behavior.

Common symptoms of dog anxiety include aggression, urinating or defecating in the house, drooling, panting, destructive behavior, depression, excessive barking, pacing, restlessness and repetitive or compulsive behaviors. Different dogs display different symptoms and combinations of symptoms when suffering from anxiety.

Canine stress is the response of dog to a demand placed upon it to change or adapt, typically exhibited as feelings of strain or pressure. Dogs experiencing stress may result in feelings of fear, agitation, hyperactivity, nervousness, oversensitivity or irritability. Negative stress, excessive stress and chronic stress can have a detrimental effect on behavior, health and overall well-being. Stress has the potential to bring on illness, suppress the immune system, cause undesirable behaviors, and increase arousal, which increases the probability of aggressive behavior.

Causes of stress in dogs include grief, exposure to conflict, excessive or insufficient stimulation, overcrowded conditions, environmental changes (schedule, people, animals, increased noise); punitive training, insufficient social time, frightening events, neglect, frustration, and uncertainty among others.

Dogs communicate that they are experiencing stress in different ways. Some indications that a dog is experiencing stress include dilated pupils, tightness around eyes, whale eye/half-moon eyes, yawning, lip/nose licking, panting, excess salivation, smiling, teeth chattering, cheek puffing, showing teeth, wrinkled muzzle, pinned back or upright ears. Other indications include tense body, stretching, excessive shedding, little or no movement, low body posture, weight shifted back, trembling/shaking, penis crowning, sweaty paws, tight brow, barking, growling, howling and whining. When stressed, a dog's behavior will often change. Common behaviors that are often stress induced include restlessness, insufficient or excessive sleeping, jumpiness/hypervigilance, irritability, excessive self-grooming, destructive behavior, loss of appetite, obsessive/compulsive behaviors, inability to focus, hyperactivity, increased urination and defecation, and vomiting and diarrhea among others.

Single nucleotide polymorphisms (SNPs) are a common type of genetic variation. SNPs are single base pair mutations at a specific locus. That is, a SNP is a difference in a single nucleotide in a DNA sequence that occurs at a specific position in a genome. Typically, for a SNP at a specific position, there are two possible nucleotide variations, which are referred to as alleles for that position. Within a population, the nucleotide variation that most commonly appears at a specific base position in a genome is referred to as the major allele; the nucleotide variation that is less common at that specific base position is referred to as the minor allele. Dogs, like most multicellular organisms have two sets of chromosomes. Thus, each dog has two copies of each gene or locus and therefore two copies of each SNP. Accordingly, for each SNP in the dog's genome, the dog may have two copies of the major allele, one minor allele and one minor allele or two minor alleles.

SNPs can act as biological markers. SNPs may be helpful in predicting drug responses and risk of developing particular diseases. SNP genotyping refers to detection of SNPs within the genome. There are numerous methods for detecting SNPs and performing SNP genotyping.

There is a need to develop improved methods to identify dogs having increased likelihood or risk of developing anxiety and stress, for methods of reducing risk of canine anxiety and stress, and for methods of treating canine anxiety and stress. There is a need for methods and compositions for reducing elevated levels of 4-EPS in canines. There is a need for methods and compositions for treating or reducing the severity of elevated levels of canine anxiety. There is a need for methods and compositions for treating or reducing the severity of elevated levels of canine stress.

BRIEF SUMMARY

Methods that comprise analyzing a biological sample obtained from the canine subject for the presence of two copies of a minor allele of the single nucleotide polymorphism BICF2P1175095 in a canine subject are provided.

The presence of two copies of the minor allele of the single nucleotide polymorphism BICF2P1175095 indicates that the canine subject has an increased likelihood of developing elevated levels of 4-ethylphenyl sulfate, an increased likelihood of developing canine stress, an increased likelihood of developing canine anxiety and/or an increased likelihood of developing inhibition of growth of beneficial microbes and promotion of growth of harmful microbes within its lifetime.

The methods may comprise analyzing a biological sample obtained from the canine subject by performing DNA sequencing, restriction enzyme digest, polymerase chain reaction (PCR), hybridization, real-time PCR, reverse transcriptase PCR, or ligase chain reaction.

The methods may comprise analyzing a biological sample obtained from the canine subject by performing at least one nucleic acid analysis technique selected from: analysis using a whole genome SNP chip, single-stranded conformational polymorphism (SSCP) assay, restriction fragment length polymorphism (RFLP), automated fluorescent sequencing; clamped denaturing gel electrophoresis (CDGE); denaturing gradient gel electrophoresis (DGGE), mobility shift analysis, restriction enzyme analysis, heteroduplex analysis, chemical mismatch cleavage (CMC), RNase protection assays, use of polypeptides that recognize nucleotide mismatches, allele-specific PCR, sequence analysis, and SNP genotyping.

The methods may comprise analyzing a biological sample obtained from the canine subject by performing at least one nucleic acid analysis technique selected from: hybridization-based methods, enzyme-based methods, post-amplification methods based on physical properties of DNA, and sequencing methods.

The methods may comprise analyzing a biological sample obtained from the canine subject by performing at least one nucleic acid analysis technique selected from: hybridization-based methods selected from the group consisting of dynamic allele-specific hybridization, molecular beacon methods and SNP microarrays; enzyme-based methods selected from the group consisting of restriction fragment length polymorphism (RFLP), PCR-based methods, Flap endonuclease, primer extension methods, 5'-nuclease and oligonucleotide ligation assay; post-amplification methods based on physical properties of DNA selected from the group consisting of single strand conformation polymorphism, temperature gradient gel electrophoresis, denaturing high performance liquid chromatography, high-resolution amplicon melting, DNA mismatch-binding proteins, SNPlex, and surveyor nuclease assay; and sequencing methods Methods of preventing or reducing elevated 4-ethylphenyl sulfate levels in a canine subject comprising detecting in a biological sample from the canine subject, the presence of two copies of a minor allele of BICF2P1175095 and administering to the canine subject a composition comprising an effective amount of tomato pomace such as by feeding the canine subject a nutritional composition comprising an effective amount of tomato pomace.

Methods of treating a canine subject for canine anxiety or canine stress in a canine subject comprising detecting in a biological sample from the canine subject, the presence of two copies of a minor allele of BICF2P1175095 and administering to the canine subject a composition comprising an effective amount of tomato pomace such as by feeding the canine subject a nutritional composition comprising an effective amount of tomato pomace.

A canine food composition is provided that comprises an amount, on a dry matter basis, of tomato pomace that is equal to 0.087 to 0.21%.

A canine food composition is provided that comprises an amount, on a dry matter basis, of tomato pomace that is equal to 0.14%.

BRIEF DESCRIPTION OF THE DRAWINGS

FIG. 1 shows a matched pair analysis using data generated in Example 2. FIG. 1 shows a comparison of levels of 4-EPS in each dog on the diet containing tomato pomace (CTRL) versus on the diet containing no tomato pomace (TEST). Results show when the dogs were fed the test food diet, which contained no tomato pomace, they had higher 4-EPS levels compared to the 4-EPS levels observed when the dog were fed the control food diet, which contained tomato pomace (P=0.04).

DETAILED DESCRIPTION

The following description of the preferred embodiment(s) is merely exemplary in nature and is in no way intended to limit the invention, its application, or uses.

As used herein and in the appended claims, the singular forms "a", "an", and "the" include plural reference unless the context clearly dictates otherwise.

As used herein, the term "companion animal" includes any non-human animal suitable for being kept as a pet by humans including without limitation, a dog, a cat, rabbit and a rodent. Specific embodiments are formulations and methods of treatment for dogs and/or cats. In one specific aspect, the present invention is directed to formulations and methods of treatment for dogs.

The term "dog" includes those dogs which are companion animals such as *Canis familiaris*, working dogs and the like. The term dog is synonymous with the term canine.

The term "cat" includes those cats which are companion animals known as domestic cats or house cats, or *Felis domesticus*. The term cat is synonymous with the term feline.

Methods are provided for treating anxiety and stress in an animal, particularly a companion animal such as a canine or feline. The methods comprise administering to the animal a combination of effective amount of tomato pomace in an effective amount. The compositions comprise tomato pomace in an effective amount. The effective amount of tomato pomace is 0.044% to 0.42% of daily nutritional intake, and in some embodiments 0.066% to 0.315% of daily nutritional intake, and in some embodiments 0.087-0.21% of daily nutritional intake, and in some embodiments 0.14%, of daily nutritional intake.

"Daily nutritional intake" and "total nutritional intake per day" refers to dry matter intake per day. That is, water weight is not included in calculating the amount of nutrition consumed per day. To the extent that food and food ingredient contain water/moisture, the dry matter represents everything in the sample other than water including protein, fiber, fat, minerals, etc. Dry matter weight is the total weight minus the weight of any water. Dry matter intake per day is calculated as the total nutritional intake per day excluding all water. For example, an amount of an ingredient equal to a specific percent of daily nutritional intake refers to the amount of that ingredient in dry matter form (i.e. excluding all water) relative to the total amount of dry matter consumed (also excluding all water) in a day. The skilled artisan would readily recognize and understand nutritional amounts and percentages expressed as dry matter amounts, dry matter weights and dry matter percentages. Since foods, whether wet, moist or dry, generally contain as certain amount of water, when calculating daily dry matter intake, the water component of such food is excluded. To calculate total daily nutritional intake, which is dry matter intake per day, water is excluded. To calculate percent of an ingredient of total daily intake on a dry matter basis, water is removed from the total intake to give total daily dry matter intake and the percent of the ingredient is based on amount of ingredient present as dry matter.

The compositions useful in the methods may be a pet food composition such as a dog food composition. Alternatively, tomato pomace in may be administered as a supplement, a treat or toy or otherwise not incorporated into the food provided to the animal for daily nutritional intake.

In some preferred embodiments, the animal is a canine and the methods comprise administering to the canine an effective amount of tomato pomace daily. The effective amount of tomato pomace administered to the canine per day is 0.044% to 0.42% of daily nutritional intake, and in some embodiments 0.066% to 0.315% of daily nutritional intake, and in some embodiments 0.087-0.21% of daily nutritional intake, and in some embodiments 0.14%, of daily nutritional intake.

Compositions and methods for the treatment of anxiety or stress in an animal, particularly in companion animals such as felines and canines, are provided. The compositions and methods are useful to treat a symptom of anxiety or stress in such animals that are in need thereof. The compositions and methods are useful to treat a symptom of anxiety or stress in such animals that have elevated levels of 4-EPS. The compositions and methods are useful to reduce elevated levels of 4-EPS in an animal that has elevated levels of 4-EPS, such as companion animals, particularly canines. In some embodiments, the compositions and methods for the treatment of canine anxiety or canine stress in a canine.

As used herein, the term "treatment" refers to eliminating, reducing the severity or preventing one or more symptoms.

As used herein, the term "anxiety" refers to anxiety, anxiety disorders and symptoms of anxiety and anxiety disorders.

As used herein, the term "stress" refers to stress, stress disorders, and symptoms of stress and stress disorders.

As used herein, the terms "treatment" with reference to anxiety refers to therapeutic and/or prophylactic activity. In a canine with symptoms of anxiety, treatment of canine anxiety refers to eliminating symptoms, arresting or reducing progression of symptoms, reducing severity of symptoms and preventing symptoms. Treatment that initially eliminate, arrests, reduces progression of or reduces severity of symptoms may continue and the continuing treatment may further eliminate, arrests, reduces progression of or reduces severity of symptoms and/or prevent return or development of symptoms or reduce severity of further development of symptoms. In some embodiments, prior to treating for canine anxiety, a canine may be identified as having symptoms of anxiety. In some embodiments, a canine may be treated for anxiety without identifying symptoms of anxiety prior to treatment. In some embodiments, prior to treatment for anxiety, a canine may be identified as being predisposed to having or developing anxiety. In some embodiments, prior to treatment for anxiety, a canine may be identified as having elevated levels of 4-EPS.

As used herein, the terms "treatment" with reference to stress and stress disorders refers to therapeutic and/or prophylactic activity. In a canine with symptoms of stress or a stress disorder, treatment of canine stress refers to eliminating symptoms, arresting or reducing progression of symptoms, reducing severity of symptoms and preventing symptoms. Treatment that initially eliminate, arrests, reduces progression of or reduces severity of symptoms may continue and the continuing treatment may further eliminate, arrests, reduces progression of or reduces severity of symptoms and/or prevent return or development of symptoms or reduce severity of further development of symptoms. In some embodiments, prior to treating for canine stress, a canine may be identified as having symptoms of stress or a stress disorder. In some embodiments, a canine may be treated for stress or a stress disorder without identifying symptoms of anxiety prior to treatment. In some embodiments, prior to treatment for stress or a stress disorder, a canine may be identified as being predisposed to having or developing stress or a stress disorder. In some embodiments, prior to treatment for stress or a stress disorder, a canine may be identified as having elevated levels of 4-EPS.

As used herein, the terms "treatment" with reference to promoting beneficial microbial growth and inhibition of harmful microbial growth refers to therapeutic and/or prophylactic activity. In a canine with reduced levels of beneficial microbes and elevated levels of harmful microbes, treatment for arresting levels of beneficial microbes and harmful microbes or promoting beneficial microbial growth and inhibiting harmful microbial growth. A canine identified as being predisposed to inhibiting beneficial microbial growth and promoting harmful microbial growth prior to initiating treatment. Treatment that initially promotes beneficial microbial growth and inhibits harmful microbial growth in an animal with elevated levels of harmful microbes and reduced levels of beneficial microbes, increases levels of beneficial microbes and decreases levels of harmful microbes to a more healthful balance and thereafter the continuing treatment maintains levels. In some embodiments, prior to treating for canine stress, a canine may be identified as having elevated levels of harmful microbes and reduced levels of beneficial microbes. In some embodiments, a canine may be treated without identifying elevated levels of harmful microbes and reduced levels of beneficial microbes in the animal.

As used herein the terms "treatment of elevated 4-EPS", "treating for elevated 4-EPS" and "treating elevated 4-EPS" refer to therapeutic and/or prophylactic activity in which 4-EPS levels are reduced. In a canine with elevated 4-EPS levels, "treatment of elevated 4-EPS", "treating for elevated 4-EPS" and "treating elevated 4-EPS" refers to reducing elevated 4-EPS levels. Treatment may lower elevated 4-EPS levels to normal, non-elevated levels or to reduced elevated 4-EPS levels. Following reduction of elevated 4-EPS levels, treatment may prevent elevation of 4-EPS levels or reduce severity of further development of elevated 4-EPS levels. In a canine that does not have elevated 4-EPS levels, "treatment of elevated 4-EPS", "treating for elevated 4-EPS" and "treating elevated 4-EPS" refers to arresting or lowering of 4-EPS levels, and preventing development of elevated 4-EPS levels or reducing severity of development of elevated 4-EPS levels. In some embodiments, prior to treating for 4-EPS, a canine may be identified as having elevated 4-EPS by measuring 4-EPS levels. In some embodiments, a canine may be treated for elevated 4-EPS without measuring 4-EPS levels prior to treatment. In some embodiments, prior to treating for 4-EPS, a canine may be identified as being predisposed to elevated 4-EPS. A canine identified as being predisposed to elevated 4-EPS may at the time of treatment have elevated 4-EPS, in which case the treatment is therapeutic, or may not have elevated 4-EPS, in which case the treatment is prophylactic, or treatment may be undertaken without determining 4-EPS levels. In some embodiments, a canine may be identified as being predisposed to elevated 4-EPS prior to initiating treatment with or without measuring 4-EPS levels.

As used herein, "an amount effective," "an effective amount," and like terms refer to that amount of tomato pomace effective to achieve a particular biological result, i.e., treatment of elevated levels of 4-EPS, anxiety, stress, and levels of beneficial and harmful microbes in the microbiome. In specific embodiments, administration of an effective amount of a composition will be for a time sufficient to effect treatment. In a particular embodiment, the method comprises administration and consumption of a composition comprising tomato pomace for a period of time sufficient to result in effective treatment and maintenance An effective amount may be based on several factors, including a dog's ideal weight, the age, gender, level of activity, the metabolizable energy of the composition, and the frequency of feeding the compositions, e.g., once, twice, or three times daily, and other compositions fed to the dog. In some embodiments an effective amount refers to an amount of tomato pomace administered so based upon total nutritional intake, the amount of tomato pomace is equal to 0.087-0.21% of total nutritional intake per day. In some embodiments an effective amount refers to a pet food comprising 0.087-0.21% tomato pomace. In some embodiments an effective amount refers to an amount of tomato pomace administered so based upon total nutritional intake, the amount of tomato pomace is equal to 0.14% of total nutritional intake per day. In some embodiments an effective amount refers to a pet food comprising 0.14% tomato pomace.

A "food," "food composition," or "pet food composition" can, in some embodiments, be a nutritionally complete diet for the animal, such as a dog, to which it is fed.

As used herein, an "ingredient" refers to any component of a composition.

The term "nutrient" refers to a substance that provides nourishment. In some cases, an ingredient may comprise more than one "nutrient," for example, a composition may comprise corn comprising important nutrients including both protein and carbohydrate.

Food compositions can be provided to an animal, such as but not limited to a pet, in the form of pet food. A variety of commonly known types of pet foods are available to pet owners. The selection of pet food includes but is not limited to wet pet food, semi-moist pet food, dry pet food and pet treats. Wet pet food generally has a moisture content greater than about 65%. Semi-moist pet food typically has a moisture content between about 20% and about 65% and may include humectants, potassium sorbate, and other ingredients to prevent microbial growth (bacteria and mold). Dry pet food such as but not limited to food kibbles generally has a moisture content below about 15%. Pet treats typically may be semi-moist, chewable treats; dry treats in any number of forms, chewable bones or baked, extruded or stamped treats; confection treats; or other kinds of treats as is known to one skilled in the art.

As used herein, the term "kibble" or "food kibble" refers to a particulate pellet like component of animal feeds, such as dog and cat feeds. In some embodiments, a food kibble has a moisture, or water, content of less than 15% by weight. Food kibbles may range in texture from hard to soft. Food kibbles may range in internal structure from expanded to dense. Food kibbles may be formed by an extrusion process or a baking process. In non-limiting examples, a food kibble may have a uniform internal structure or a varied internal structure. For example, a food kibble may include a core and a coating to form a coated kibble. It should be understood that when the term "kibble" or "food kibble" is used, it can refer to an uncoated kibble or a coated kibble.

As used herein, the term "extrude" or "extrusion" refers to the process of sending preconditioned and/or prepared ingredient mixtures through an extruder. In some embodiments of extrusion, food kibbles are formed by an extrusion processes wherein a kibble dough, including a mixture of wet and dry ingredients, can be extruded under heat and pressure to form the food kibble. Any type of extruder can be used, examples of which include but are not limited to single screw extruders and twin-screw extruders. The list of sources, ingredients, and components as described hereinafter are listed such that combinations and mixtures thereof are also contemplated and within the scope herein.

As contemplated herein, compositions are meant to encompass, but not be limited to, nutritionally-complete and balanced animal food compositions. A "nutritionally complete diet" is a diet that includes sufficient nutrients for maintenance of normal health of a healthy dog on the diet. Nutritionally complete and balanced pet food compositions, e.g., for canines, are familiar to one of skill in the art. For example, substances such as nutrients and ingredients suitable for nutritionally complete and balanced animal feed compositions, and recommended amounts thereof, may be found for example, in the Official Publication of the Association of American Feed Control Officials, Inc. (AAFCO), Atlanta, Ga., (2012).

It is contemplated that in feeding a dog a diet comprising an effective amount of tomato pomace, a preferred method comprises feeding the dog a pet food that contains tomato pomace as an ingredient. In other embodiments, feeding a dog a diet comprising an effective amount of tomato pomace is achieved by administering the dog tomato pomace as a supplement or treat. Whether delivered in a pet food composition or as a separate supplement or in a treat, providing the dog with the tomato pomace by any means is considered feeding a dog a diet comprising an effective amount of tomato pomace.

As used herein, the term "supplement(s)" include, but are not limited to, a feed used with another feed to improve nutritive balance or performance of the total diet for an animal. Supplements include, but are not limited to, compositions that are fed undiluted as a supplement to other feeds, offered free choice with other parts of an animal's ration that are separately available, or diluted and mixed with an animal's regular feed to produce a complete feed. The AAFCO guidelines, for example, contain a discussion relating to supplements in the Official Publication of the Association of American Feed Control Officials, Inc. (AAFCO), Atlanta, Ga. (2012). Supplements may be in various forms including, for example, powders, liquids, syrups, pills, encapsulated compositions and the like A diet may comprise tomato pomace in an effective amount to reduce elevated levels of 4-EPS in a canine. A diet that comprises tomato pomace is useful to treat anxiety in a canine. A diet that comprises tomato pomace is useful to treat stress in a canine. A diet that comprises tomato pomace is useful to promote of beneficial microbial growth and inhibit harmful microbial growth in the canine subject's microbiome, particularly in the gastrointestinal track.

Genetic Predisposition for Elevated 4-EPS

Genetic association studies revealed a genetic marker that can be used identify dogs as being predisposed to develop elevated levels of 4-EPS. The genetic marker is a SNP located upstream from the NOD1 gene at chr14:43309715 using the CanFam3.1 reference genome is referred to on the commercial Illumina Canine genotyping array as BICF2P1175095. Dogs that are homozygous for the minor allele of SNP BICF2P1175095 are predisposed to develop elevated levels of 4-EPS. The minor allele of SNP BICF2P1175095 is C. Dogs have 39 pairs of chromosomes. Dogs that are homozygous for the minor allele of SNP BICF2P1175095 have the minor allele present on each of the two chromosome 14s in the chromosome 14 pair. Dogs that are homozygous for the minor allele are said to have the homozygous minor allele genotype, which is genotype CC for SNP BICF2P1175095, or as used in herein genotype CC. Dogs that have the CC genotype have an increased likelihood of developing elevated levels of 4-EPS, canine anxiety and canine stress. In addition to predisposing the canine to developing elevated levels of 4-EPS, anxiety and stress, the CC genotype in dogs that have an elevated likelihood of inhibition of beneficial microbial growth in the canine subject's microbiome, particularly the microbiome of the gastrointestinal track, and promotion of harmful microbial growth in the canine subject's microbiome, particularly the microbiome of the gastrointestinal track.

A dog that is identified as being predisposed to develop elevated levels of 4-EPS, such as be identifying the dog as having the CC genotype, can be treated through diet that comprises an effective amount of tomato pomace.

Identifying the CC genotype in a canine subject identifies the canine subject as being predisposed to elevated levels of 4-EPS. Identifying the CC genotype in a canine, identifies the canine as being predisposed to anxiety. Identifying the CC genotype in a canine, identifies the canine as being predisposed to stress. Identifying the CC genotype in a canine, identifies the canine as being predisposed to inhibition of beneficial microbial growth and thus reduced levels of beneficial microbes in the canine subject's microbiome, particularly the microbiome of the gastrointestinal track, and as being predisposed to promotion of harmful microbial growth and thus increased levels of harmful microbes, in the canine subject's microbiome, particularly the microbiome of the gastrointestinal track.

A diet that comprises tomato pomace in an effective amount to reduce elevated levels of 4-EPS in a canine is particularly beneficial to a canine subject which has with the CC genotype and is accordingly predisposed to elevated levels of 4-EPS. A diet that comprises an effective amount of tomato pomace is particularly beneficial to a canine subject which has with the CC genotype and is accordingly predisposed to experiencing anxiety. A diet that comprises an effective amount of tomato pomace is particularly beneficial to a canine subject which has with the CC genotype and is accordingly predisposed to experiencing stress. A diet that comprises an effective amount of tomato pomace in an effective amount to is particularly beneficial to a canine subject which has with the CC genotype and is accordingly predisposed to inhibition of beneficial microbial growth and promotion of harmful microbial growth in the canine subject's microbiome, particularly the microbiome of the gastrointestinal track.

Without being bound to any particular theory, the CC genotype for BICF2P1175095, which is located upstream from the NOD1 gene, may result in conditions in the gastrointestinal track of a canine that favor harmful microbial growth over beneficial microbial growth. As a result, beneficial microbial growth is inhibited in the microbiome of the canine's gastrointestinal track, and harmful microbial growth is promoted in the microbiome of the canine's gastrointestinal track, resulting in decreased levels of beneficial microbes and increased levels of harmful microbes. The harmful microbes of the microbiome release the metabolic toxin 4-EPS, resulting elevated levels of circulating 4-EPS in the canine. The elevated levels of circulating 4-EPS in the canine can result in development of anxiety and/or stress in the dog. A diet comprising an effective amount of tomato pomace may result in increased levels of beneficial microbes and decreased levels of harmful microbes in the canine's microbiome. The increased levels of beneficial microbes and decreased levels of harmful microbes in the canine's microbiome results in less 4-EPS released into the circulation, thereby reducing 4-EPS levels.

Methods of identifying a canine subject predisposed to elevated levels of 4-EPS comprise determining that the canine subject has the CC genotype. Methods of identifying a canine subject predisposed to anxiety comprise determining that the canine subject has the CC genotype. Methods of identifying a canine subject predisposed to stress comprise determining that the canine subject has the CC genotype. Methods of identifying a canine subject predisposed to inhibiting beneficial microbial growth and promoting harmful microbial growth in the microbiome, particularly in the gastrointestinal track, comprise determining that the canine subject has the CC genotype.

Methods of reducing elevated 4-EPS levels and preventing elevated 4-EPS levels or reducing the severity of elevated 4-EPS levels in a canine subject comprise feeding the canine subject a diet that comprises tomato pomace in an effective amount reduce elevated 4-EPS levels, prevent elevated 4-EPS levels the reduce the severity of elevated 4-EPS levels. In some embodiments, methods of reducing elevated 4-EPS levels and preventing elevated 4-EPS levels or reducing the severity of elevated 4-EPS levels in a canine subject comprise identifying the canine subject as having the CC genotype and feeding the canine subject a diet that comprises tomato pomace in an effective amount reduce elevated 4-EPS levels, prevent elevated 4-EPS levels the reduce the severity of elevated 4-EPS levels.

Methods of alleviating, reducing and/or preventing anxiety in a canine subject comprise feeding the canine subject a diet that comprises tomato pomace in an effective amount to alleviate, reduce and/or prevent anxiety and symptoms of anxiety disorders in the canine. In some embodiments, methods of alleviating, reducing and/or preventing anxiety in a canine subject comprise identifying the canine subject as having the CC genotype and feeding the canine subject a diet that comprises tomato pomace in an effective amount to alleviate, reduce and/or prevent anxiety in the canine.

Methods of alleviating, reducing and/or preventing stress in a canine subject comprise feeding the canine subject a diet that comprises tomato pomace in an effective amount to alleviate, reduce and/or prevent stress in the canine. In some embodiment, methods of alleviating, reducing and/or preventing stress in a canine subject comprise identifying the canine subject as having the CC genotype and feeding the canine subject a diet that comprises tomato pomace in an effective amount to alleviate, reduce and/or prevent stress in the canine.

Methods of promoting beneficial microbial growth and inhibiting harmful microbial growth in a canine subject comprise feeding the canine subject a diet that comprises an effective amount tomato pomace to promoting beneficial microbial growth and inhibiting harmful microbial growth. In some embodiments, methods of promoting beneficial microbial growth and inhibiting harmful microbial growth in a canine subject comprise identifying the canine subject as having the CC genotype and feeding the canine subject a diet that comprises effective amount tomato pomace to promoting beneficial microbial growth and inhibiting harmful microbial growth.

The methods comprise analyzing a biological sample obtained from the canine subject for the presence of 2 copies of the minor allele C of the single nucleotide polymorphism it is located at chr14:43309715 as referred to in the CanFam3.1 reference genome. The SNP is named BICF2P1175095 on the commercial Illumina Canine genotyping array. That is, methods comprise analyzing a biological sample obtained from the canine subject for the presence of the CC genotype. In some embodiments, the sample is analyzed by performing DNA sequencing, restriction enzyme digest, polymerase chain reaction (PCR), hybridization, real-time PCR, reverse transcriptase PCR, or ligase chain reaction A canine subject having 2 copies of the minor allele C of the SNP located at chr14:43309715 (BICF2P1175095) present, i.e. a canine subject has the CC genotype, is predisposed to developing elevated 4-EPS levels within its lifetime. The CC genotype indicates that the canine subject is predisposed to developing anxiety within its lifetime, that the canine subject is predisposed to developing stress within its lifetime, and that the canine subject is predisposed to inhibit beneficial microbial growth and promote harmful microbial growth in its microbiome.

An increased likelihood of developing elevated levels of 4-ethylphenyl sulfate indicates an increased likelihood of developing canine anxiety, an increased likelihood of developing canine stress and/or an increased likelihood of inhibiting beneficial microbial growth and promoting harmful microbial growth. Methods of identifying a canine as being at an increased likelihood of developing elevated levels of 4-ethylphenyl sulfate are methods of identifying a canine as being at an increased likelihood of developing canine anxiety, as being at an increased likelihood of developing canine stress, and/or as being at an increased likelihood of inhibiting beneficial microbial growth and promoting harmful microbial growth.

In canines exhibiting symptoms of canine stress or canine anxiety, the methods provided herein that comprise analyzing a biological sample obtained from the canine subject for the presence of 2 copies of the minor allele C of the single nucleotide polymorphism it is located at chr14:43309715 as referred to in the CanFam3.1 reference genome as part of the method to diagnose the canine as having the genetic predisposition to have canine stress or canine anxiety.

Methods of identifying canines as having an increased likelihood of developing elevated levels of 4-ethylphenyl sulfate indicates an increased likelihood of developing canine anxiety, an increased likelihood of developing canine stress and/or an increased likelihood of inhibiting beneficial microbial growth and promoting harmful microbial growth that comprise analyzing a biological sample obtained from the canine subject for the presence of 2 copies of the minor allele C of the single nucleotide polymorphism it is located at chr14:43309715 as referred to in the CanFam3.1 reference genome may be part of methods to treat the canine to prevent or reduce elevated levels of 4-ethylphenyl sulfate, to prevent or alleviate symptoms of canine anxiety, to prevent or alleviate symptoms of an increased likelihood of developing canine stress and/or to prevent or reduce inhibition of beneficial microbial growth and promotion of harmful microbial growth.

Methods of identifying canines with a genetic predisposition for developing elevated levels of 4-ethylphenyl sulfate, developing canine anxiety, developing canine stress and/or having increased likelihood of inhibiting beneficial microbial growth and promoting harmful microbial growth that comprise analyzing a biological sample obtained from the canine subject that exhibits symptoms of canine stress or canine anxiety for the presence of 2 copies of the minor allele C of the single nucleotide polymorphism it is located at chr14:43309715 as referred to in the CanFam3.1 reference genome may be part of methods to treat the canine to reduce elevated levels of 4-ethylphenyl sulfate, to alleviate symptoms of canine anxiety, to alleviate symptoms of an increased likelihood of developing canine stress and/or to prevent or reduce inhibition of beneficial microbial growth and promotion of harmful microbial growth.

Single Nucleotide Polymorphism BICF2P1175095

As noted above, SNP BICF2P1175095, is located at chromosome 14, position 43309715 in the CanFam3.1 reference genome (chr14:43309715). SEQ ID NO:1 is 201 nucleotides and shows the sequence that includes the SNP BICF2P1175095 (chr14:43309715) and the 100 nucleotides flanking upstream and 100 nucleotides flanking downstream of the SNP. Position 101 of SEQ ID NO:1 is the position of the SNP; the minor allele is C and the major allele is A are shown as [C/A].

```
201 nucleotides:
                                            SEQ ID NO: 1
5' TATTTGTCTT GAAATTTCAT TATAAGCTTA ATTTTTCCTT

GTTGTTGGTA TCAGACTACC GTGTATGCTT GTTTTCTGTT

TCCCTCCACG GCAATCTACC [C/A]AAATAAAAT GAGGTGTGGT

TCCTTTGTCC TTTCTGTAAC TCTCAGTCCT CCCCCCCACC

CCATATCCTT TACTTGAGGA GGGAGACTAC ATCTAATTTG G-3'
```

Genomic sequences containing the disclosed SNP can be accessed in a number of ways. One way is to refer to the Illumina canine HD annotation file found at <ftp://webdata2:webdata2@ussdftp.illumina.com/downloads/ProductFiles/CanineHD/CanineHD_B.csv>. In addition, the chromosome and location defined by the Dog reference genome CanFam3.1 for the SNP is chr14:43309715. Those skilled in the art can use a publicly available interface such as the University of California Santa Cruz Genome browser to locate the SNP of interest and extract the flanking DNA sequences using genome browser tools. Furthermore, the dog reference Genome is publicly available from numerous sources such as <ftp://ftp.ensembl.org/pub/release-94/fasta/canis_familiaris/dna/> or <http://hgdownload.cse.ucsc.edu/goldenPath/canFam3/bigZips/> or <ftp://ftp.ncbi.nlm.nih.gov/genomes/all/GCA/000/002/285/GCA_000002285.2_CanFam3.1>. These databases can be used to extract the relevant DNA sequences.

Methods of detecting the CC genotype which is associated with an increased likelihood of developing elevated levels of 4-EPS in a canine subject are provided. Methods of identifying dogs at increased risk for developing anxiety, stress and reduced levels of beneficial microbes and increased levels of harmful microbes are provided.

In some embodiments, the sample is a genomic DNA sample. In some embodiments, the sample is obtained from blood, saliva, follicle root, nasal swab or oral swab of the canine subject. In some embodiments, the biological sample is a genomic DNA sample from the canine subject using the commercially available kit such as PERFORMAgene PG-100 Oral sample collection it (DNA Genotek, OraSure Technologies, Inc., Bethlehem, Pa.).

In some embodiments, methods comprise detecting the CC genotype. That is, the methods comprise detecting the presence 2 copies of the minor allele C of SNP BICF2P1175095 (chr14:43309715). In some embodiments, detecting the presence 2 copies of the minor allele C of SNP BICF2P1175095 (chr14:43309715) comprises interrogating a DNA sample from the canine for the presence of the minor allele C and the major allele A and detecting the presence of the minor allele and the absence of the major allele A. The detection of minor allele but not the major allele in effect detects the presence of 2 copies of the minor allele.

In some embodiments, the method of detecting the presence 2 copies of the minor allele C of SNP BICF2P1175095 (chr14:43309715), comprises interrogating a DNA sample from the canine for the presence of the major allele and detecting zero copies of the major allele. The detection of zero copies of the major allele in effect detects the presence of 2 copies of the minor allele. That is, looking for the major allele and finding no copies in effect detects the presence of 2 copies of the minor allele.

In some embodiments, the CC genotype is detected using methods that include at least one nucleic acid analysis technique selected from: DNA sequencing, restriction enzyme digest, polymerase chain reaction (PCR), hybridization, real-time PCR, reverse transcriptase PCR, or ligase chain reaction.

In some embodiments, the CC genotype is detected by performing at least one nucleic acid analysis technique selected from the group consisting of: analysis using a whole genome SNP chip; single-stranded conformational polymorphism (SSCP) assay; restriction fragment length polymorphism (RFLP); automated fluorescent sequencing; clamped denaturing gel electrophoresis (CDGE); denaturing gradient gel electrophoresis (DGGE); mobility shift analysis; restriction enzyme analysis; heteroduplex analysis; chemical mismatch cleavage (CMC); RNase protection assays; use of polypeptides that recognize nucleotide mismatches; allele-specific PCR; sequence analysis; and SNP genotyping.

In some embodiments, the CC genotype is detected using a method selected from the types of methods consisting of: hybridization-based methods, enzyme-based methods, post-amplification methods based on physical properties of DNA, and sequencing methods.

In some embodiments, the CC genotype is detected using a method selected from the types of methods consisting of: hybridization-based methods selected from the group consisting of: dynamic allele-specific hybridization, molecular beacon methods and SNP microarrays; enzyme-based methods selected from the group consisting of: restriction fragment length polymorphism (RFLP), PCR-based methods, Flap endonuclease, primer extension methods, 5'-nuclease and oligonucleotide ligation assay; post-amplification methods based on physical properties of DNA selected from the group consisting of: single strand conformation polymorphism, temperature gradient gel electrophoresis, denaturing high performance liquid chromatography, high-resolution amplicon melting, DNA mismatch-binding proteins, SNPlex, and surveyor nuclease assay; and sequencing methods In some embodiment, the CC genotype is detected using a high-density array that contains genetic markers including the genetic markers for interrogating the SNP.

In some embodiment, the CC genotype is detected using a low-density array that contains genetic markers for interrogating the SNP.

In some embodiment, the CC genotype is detected using a high-density array containing genetic markers. Examples of arrays include the commercially available microarrays such as the GeneChip® Canine Genome 2.0 Array (Affymetrix, Thermo Fisher Scientific, Waltham, Mass.), Dog Genome Microarray (Core Life Sciences, Irvine Calif.), the Illumina Canine HD panel and an additional 50,000-100,000 custom genetic markers (SNPs) (The Illumina Canine HD panel and an additional 50,000-100,000 custom genetic markers (SNPs) such as Infinium® iSelect® Custom Genotyping Assays (Illumina, Inc. San Diego, Calif.).

In some embodiments, the MassARRAY System is used in the detection of the presence of the CC genotype. The MassARRAY System is a non-fluorescent detection platform utilizing mass spectrometry to accurately measure PCR-derived amplicons. Mass spectrometry, coupled with end point PCR, enables highly multiplexed reactions under universal cycling conditions to provide accurate, rapid, and cost-effective analysis. The MassARRAY System offers a unique solution for targeted genetic testing with limited input material.

In some embodiments, bead array technology is used in the detection of the CC genotype is detected. For example, the Illumina BeadArray technology and the Infinium HD assay (Illumina, Inc. San Diego, Calif.) may be used. In some embodiments, bead array technology is used in the detection of the presence of SNP alleles. The Illumina BeadArray technology is based on small silica beads that self-assemble in microwells on planar silica slides. Each bead is covered with hundreds of thousands of copies of a specific oligonucleotide that act as a capture sequence in the Infinium assay. Once the beads have self-assembled, a proprietary decoding process maps the location of every bead, ensuring that each one is individually quality controlled. The result of this manufacturing process is that every BeadChip undergoes rigorous testing to assure the highest possible quality standards. The Infinium assay can be scaled to unlimited multiplexing without compromising data quality, unlike many alternative PCR-dependent assays. The simple streamlined workflow is common across all products, no matter how many SNPs are being interrogated. Likewise, the data acquisition process and analysis are the same. The Infinium assay protocol features single-tube sample preparation and whole genome amplification without PCR or ligation steps significantly reducing labor and sample handling errors. After hybridizing unlabeled DNA sample on the Beadchip, two-step allele detection provides high call rates and accuracy. Selectivity and specificity are accomplished in two-steps. Target hybridization to bead-bound 50-mer oligos provides high selectivity while enzymatical single-base extension also incorporates a labeled nucleotide for assay readout. The staining reagent is optimized to provide a higher signal, and more balanced intensities between red and green channels. These features contribute to accuracy, high call rates and copy number data with low noise. The Infinium assay produces two-color readouts (one color for each allele) for each SNP in a genotyping study. Intensity values for each two-color channels, A and B, convey information about the allelic ratio at a single genomic locus. Typical studies incorporate values for a large number of samples (hundreds to tens of thousands) to ensure significant statistical representation. When these values are appropriately normalized and plotted distinct patterns (or clusters) emerge, in which samples have identical genotypes at an assayed locus exhibit similar signal profiles (A and B values) and aggregate in clusters. For diploid organisms, bi-allelic loci are expected to exhibit three clusters (AA, AB and BB). Genotype calls are based upon information derived from standard cluster file, which provides statistical data from a representative sample set. This enables genotypes to be called by referencing assay single intensities against known data for a given locus. Since the call accuracy is tied to the quality of the cluster data, having efficient and robust clustering algorithm is essential for accurate genotyping. The Illumina Gebtrain2 algorithm accurately and efficiently identifies cluster patters of genotyping samples and reports summary.

SNP alleles may be detected using hybridization-based methods. Examples of hybridization-based methods include dynamic allele-specific hybridization, methods that employ molecular beacons, and methods that employ SNP microarrays including high-density oligonucleotide SNP arrays or low-density oligonucleotide SNP arrays. SNPs can be interrogated by hybridizing complementary DNA probes to the SNP site. In dynamic allele-specific hybridization, a genomic segment is amplified and attached to a bead through a PCR reaction with a biotinylated primer. The amplified product is then attached to a streptavidin column and washed to remove the unbiotinylated strand. An allele-specific oligonucleotide is then added in the presence of a molecule that fluoresces when bound to double-stranded DNA. The intensity is measured as temperature is increased until the melting temperature (Tm) can be determined. SNP are detected by their lower than expected Tm. Specifically engineered single-stranded oligonucleotide probes are used in SNP detection that uses molecular beacons. Oligonucleotides are designed in which complementary regions are at each end and a probe sequence is located in between such that probe take on a hairpin, or stem-loop, structure in its natural, isolated state. A fluorophore is attached to one end of the probe a fluorescence quencher is attached to the other end. The fluorophore is in close proximity to the quencher when the oligo is in a hairpin configuration and the molecule does not emit fluorescence. The probe sequence is complementary to the genomic DNA used in the assay. If the probe sequence of the molecular beacon encounters its target genomic DNA during the assay, it will anneal and hybridize. The oligo will no longer assume the hairpin configuration and will fluoresce. High-density oligonucleotide SNP arrays comprise hundreds of thousands of probes arrayed on a small chip, allowing for many SNPs to be interrogated simultaneously. Several redundant probes designed to have the SNP site in several different locations as well as containing mismatches to the SNP allele are used to interrogate each SNP. The differential amount of hybridization of the target DNA to each of these redundant probes, allows for specific homozygous and heterozygous alleles to be determined.

The CC genotype may be detected using enzyme-based methods. A broad range of enzymes including DNA ligase, DNA polymerase and nucleases may be employed. Examples of enzyme-based methods include methods based upon restriction fragment length polymorphism (RFLP), PCR-based methods, methods that utilize Flap endonuclease; methods that utilize primer extension, methods that utilize 5'-nuclease and methods that include oligonucleotide ligation assays. RFLP methods to detect SNPs use many different restriction endonucleases to digestion a genomic sample. It is possible to ascertain whether or not the enzymes cut the expected restriction sites by determining fragment lengths through a gel assay. RFLP assays are designed to include enzymes that cut in the presence or absence of SNPs and the pattern of fragment lengths can be used to determine the presence or absence of SNPs. PCR based methods include tetra-primer amplification refractory mutation system PCR, or ARMS-PCR, and multiple qPCR reactions. Tetra-primer amplification refractory mutation system PCR, or ARMS-PCR, employs two pairs of primers to amplify two alleles in one PCR reaction. The primers are designed such that the two primer pairs overlap at a SNP location but each match perfectly to only one of the possible SNPs. Alternatively, multiple qPCR reactions can be run with different primer sets that target each allele separately. Some embodiments utilize Flap endonuclease (FEN), which is an endonuclease that catalyzes structure-specific cleavage. This cleavage is highly sensitive to mismatches and can be used to interrogate SNPs with a high degree of specificity. A FEN called cleavase is combined with two specific oligonucleotide probes, that together with the target DNA, can form a tripartite structure recognized by cleavase. The first probe, called the Invader oligonucleotide is complementary to the 3' end of the target DNA. The last base of the Invader oligonucleotide is a non-matching base that overlaps the SNP nucleotide in the target DNA. The second probe is an allele-specific probe which is complementary to the 5' end of the target DNA, but also extends past the 3' side of the SNP nucleotide. The allele-specific probe will contain a base complementary to the SNP nucleotide.

Primer extension is a two-step process that first involves the hybridization of a probe to the bases immediately upstream of the SNP nucleotide followed by a 'mini-sequencing' reaction, in which DNA polymerase extends the hybridized primer by adding a base that is complementary to the SNP nucleotide. This incorporated base is detected and determines the SNP allele. The primer extension method is used in a number of assay formats. These formats use a wide range of detection techniques that include MALDI-TOF Mass spectrometry (see Sequenom) and ELISA-like methods. Sequenom's iPLEX SNP genotyping method, which uses a MassARRAY mass spectrometer. The flexibility and specificity of primer extension make it amenable to high throughput analysis. Primer extension probes can be arrayed on slides allowing for many SNPs to be genotyped at once. Referred to as arrayed primer extension (APEX), this technology has several benefits over methods based on differential hybridization of probes.

Illumina Incorporated's Infinium assay is an example of a whole-genome genotyping pipeline that is based on primer extension method. In the Infinium assay, over 100,000 SNPs can be genotyped. The assay uses hapten-labelled nucleotides in a primer extension reaction. The hapten label is recognized by antibodies, which in turn are coupled to a detectable signal. APEX-2 is an arrayed primer extension genotyping method which is able to identify hundreds of SNPs or mutations in parallel using efficient homogeneous multiplex PCR (up to 640-plex) and four-color single-base extension on a microarray. The multiplex PCR requires two oligonucleotides per SNP/mutation generating amplicons that contain the tested base pair. Methods that utilize 5'-nuclease include methods using Taq DNA polymerase's 5'-nuclease activity in the TaqMan assay for SNP genotyping. The TaqMan assay is performed concurrently with a PCR reaction and the results can be read in real-time as the PCR reaction proceeds. In methods that include oligonucleotide ligation assays, oligonucleotide DNA ligase catalyzes the ligation of the 3' end of a DNA fragment to the 5' end of a directly adjacent DNA fragment. This mechanism can be used to interrogate a SNP by hybridizing two probes directly over the SNP polymorphic site, whereby ligation can occur if the probes are identical to the target DNA. Examples of other post-amplification methods for detecting SNPs include methods based upon DNA's physical properties. Such methods first involve PCR amplification of the target DNA.

Several methods of detecting SNP alleles are based upon DNA's physical properties such as melting temperature and single stranded conformation. Methods that use single stranded conformation are based upon single-stranded DNA (ssDNA) that folds into a tertiary structure. The conformation is sequence dependent and most single base pair mutations will alter the shape of the structure. When applied to a gel, the tertiary shape will determine the mobility of the ssDNA, providing a mechanism to differentiate between SNP alleles. This method first involves PCR amplification of the target DNA. The double-stranded PCR products are denatured using heat and formaldehyde to produce ssDNA. The ssDNA is applied to a non-denaturing electrophoresis gel and allowed to fold into a tertiary structure. Differences in DNA sequence will alter the tertiary conformation and be detected as a difference in the ssDNA strand mobility. Temperature gradient gel electrophoresis (TGGE) or temperature gradient capillary electrophoresis (TGCE) methods are based on the principle that partially denatured DNA is more restricted and travels slower in a gel or other porous material. In another method, denaturing high performance liquid chromatography (DHPLC) uses reversed-phase HPLC to interrogate SNPs. In DHPLC, the solid phase which has differential affinity for single and double-stranded DNA. Another method used is high-resolution melting of the entire amplicon. Use of DNA mismatch-binding proteins may also be used to detect SNPs. MutS protein from *Thermus aquaticus* binds different single nucleotide mismatches with different affinities and can be used in capillary electrophoresis to differentiate all six sets of mismatches. SNPlex is a proprietary genotyping platform sold by Applied Biosystems. Surveyor nuclease assay uses surveyor nuclease, a mismatch endonuclease enzyme that recognizes all base substitutions and small insertions/deletions (indels), and cleaves the 3' side of mismatched sites in both DNA strands. Sequencing technologies can also be used in SNP detection. Advances in sequencing technology allow SNP detection by sequencing more practical.

Genotyping by sequencing using next generation sequencing technologies has become a common practice. Genotyping by sequencing, also called GBS, is a method to discover single nucleotide polymorphisms (SNP) in order to perform genotyping studies, such as genome-wide association studies (GWAS). GBS uses restriction enzymes to reduce genome complexity and genotype multiple DNA samples. After digestion, PCR is performed to increase fragments pool and then GBS libraries are sequenced using next generation sequencing technologies. With the advancement of next generation sequencing technologies such as Illumina short read sequencing by synthesis and PacBio's single molecule real time sequencing it is becoming more feasible to do GBS. In the future, development of new technologies such as nanopore single molecule sequencing may allow whole genome sequencing/genotyping.

Compositions and Formulations

Application of the methodology outlined above has identified bioactive dietary components that have been combined to provide compositions, foods, and diets that provide significant benefits to dogs identified as being predisposed to elevated levels of 4-EPS and thus at an increased risk of developing anxiety, an increased risk of developing anxiety stress and an increased risk of inhibiting beneficial microbial growth and promoting harmful microbial growth in the canine's microbiome, in particular the gut microbiome.

Methods are provided that comprise feeding a dog a daily diet that comprises tomato pomace in an amount equal to 0.044% to 0.42% of total nutritional intake per day. In some embodiments, the methods provided comprise feeding a dog a daily diet that comprises tomato pomace in an amount equal to 0.066% to 0.315% of total nutritional intake per day. In some embodiments, the methods provided comprise feeding a dog a daily diet that comprises tomato pomace in an amount equal to 0.087% to 0.21% of total nutritional intake per day. In some embodiments, the methods provided comprise feeding a dog a daily diet that comprises tomato pomace in an amount equal to 0.14% of total nutritional intake per day.

In some embodiments, the food product is a nutritionally complete diet for an adult canine. In a specific aspect, the food product is a nutritionally complete diet formulated for an adult companion canine.

In some embodiments, the compositions include food compositions that may comprise an effective amount of tomato pomace in combination with protein in an amount from 4% to 75% or more based on the total weight of the composition on a dry matter basis, fat in an amount from 5% to 50% or more based on the total weight of the composition on a dry matter basis, and carbohydrate from 5% to 75% or more based on the total weight of the composition on a dry matter basis, wherein the food composition is suitable for consumption by a dog.

The compositions, which are administered in methods provided herein, may be formulated as a food composition that, in certain embodiments, is a nutritionally-balanced and/or nutritionally-complete food product or diet. In other embodiments, the composition is formulated and prepared as a nutritional supplement, a treat, or a toy.

In some embodiments, for example, in addition to an effective amount of tomato pomace, a nutritionally complete and balanced dog food composition may comprise: from 4% to 90%, from 5% to 75%, from 10% to 60% protein, and from 15% to 50% by weight of protein; from 0% to 90%, from 2% to 80%, from 5% to 75%, and from 10% to 50% by weight of carbohydrate; from 2% to 60%, from 5% to 50%, and from 10% to 35% by weight of fat. The compositions may further contain from 0 to 15% or from 2% to 8%, by weight of vitamins and minerals, antioxidants, and other nutrients which support the nutritional needs of the animal.

Sources of proteins, carbohydrates, fats, vitamins, minerals, balancing agents, and the like, suitable for inclusion in the compositions, and particularly in the food products to be administered in methods provided herein, may be selected from among those conventional materials known to those of ordinary skill in the art.

In some embodiments, proteins useful as ingredients of the food compositions may comprise proteins from animal sources, such as animal proteins, including mammalian, avian protein, reptilian, amphibian, fish, invertebrate proteins and combinations thereof, e.g., from any of cattle, sheep, pig, goat, deer, rabbit, horse, kangaroo, their milk, curds, whey or blood, and internal tissues and organs such as smooth muscle, striate muscle, liver, kidney, intestine or heart; additional avian protein sources encompass turkey, goose, duck, ostrich, quail, pigeon, their eggs and internal tissues and organs such as smooth muscle, striate muscle, liver, kidney, intestine or heart; amphibian sources include frog or salamander, reptilian protein sources include alligator, lizard, turtle and snake; a fish protein sources include catfish, herring, salmon, tuna, bluefish, cod, halibut, trout, swordfish and their eggs; and an invertebrate protein sources include lobster, crab, clams, mussels or oysters, and combinations thereof, meat protein isolate, whey protein isolate, egg protein, mixtures thereof, and the like, as well as vegetable sources, such as soy protein isolate, corn gluten meal, wheat gluten, mixtures thereof, and the like.

In some embodiments, carbohydrates useful as ingredients of the food compositions may include but are not limited to, one or more of corn, whole yellow corn, grain sorghum, wheat, barley, rice, millet, brewers rice, oat groats, and polysaccharides (e.g., starches and dextrins) and sugars (e.g., sucrose, lactose, maltose, glucose, and fructose) that are metabolized for energy when hydrolyzed. Examples of additional carbohydrate sources suitable for inclusion in the compositions disclosed herein include, fruits and non-tomato pomace vegetables.

Fats useful as ingredients of the food compositions may be from any source, such as but not limited to poultry fat, beef tallow, lard, choice white grease, soybean oil, corn oil, canola oil, sunflower oil, mixtures thereof, and the like. The fat may be incorporated completely within the food composition, deposited on the outside of the food composition, or a mixture of the two methods.

In some embodiments, the compositions further include an effective amount of one or more substances selected from the group consisting of glucosamine, chondroitin, chondroitin sulfate, methylsulfonylmethane ("MSM"), creatine, antioxidants, *Perna canaliculata*, omega-3 fatty acids, omega-6 fatty acids and mixtures thereof.

In some embodiments, the food composition further comprises one or more amino acid such as but not limited to arginine, histidine, isoleucine, leucine, lysine, methionine (including DL-methionine, and L-methionine), phenylalanine, threonine, tryptophan, valine, taurine, carnitine, alanine, aspartate, cystine, glutamate, glutamine, glycine, proline, serine, tyrosine, and hydroxyproline.

In some embodiments, the food composition further comprises one or more fatty acids such as but not limited to lauric acid, myristic acid, palmitic acid, palmitoleic acid, margaric acid, margaroleic acid, stearic acid, oleic acid, linoleic acid, g-linolenic acid, a-linolenic acid, stearidonic acid, arachidic acid, gadoleic acid, DHGLA, arachidonic acid, eicossatetra acid, EPA, behenic acid, erucic acid, docosatetra acid, and DPA.

In some embodiments, the food composition further comprises one or more macro nutrients such as but not limited to moisture, protein, fat, crude fiber, ash, dietary fiber, soluble fiber, insoluble fiber, raffinose, and stachyose.

In some embodiments, the food composition further comprises one or more micro nutrients such as but not limited to beta-carotene, alpha-lipoic acid, glucosamine, chondroitin sulfate, lycopene, lutein, and quercetin.

In some embodiments, the food composition further comprises one or more minerals such as but not limited to calcium, phosphorus, potassium, sodium, chloride, iron, copper, copper, manganese, zinc, iodine, selenium, selenium, cobalt, sulfur, fluorine, chromium, boron, and oxalate.

In some embodiments, the food composition further comprises one or more other vitamins, such as but not limited to vitamin A, vitamin C, vitamin D, vitamin E, *quinoa* grain, thiamine, riboflavin, niacin, pyridoxine, pantothenic acid, folic acid, vitamin B12, biotin, and choline.

In some embodiments, the food composition further comprises fiber, which may be supplied from a variety of sources, including, for example, vegetable fiber sources such as cellulose, beet pulp, peanut hulls, and soy fiber.

In some embodiments, the food composition further comprises stabilizing substances, for example, substances that tend to increase the shelf life of the composition. Potentially suitable examples of such substances include, for example, preservatives, antioxidants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

In some embodiments, the food composition further comprises additives for coloring, palatability, and nutritional purposes include, for example, colorants; iron oxide, sodium chloride, potassium citrate, potassium chloride, and other edible salts; vitamins; minerals; and flavoring. The amount of such additives in a composition typically is up to 5% (dry basis of the composition).

Preparation of Compositions

The compositions that comprise tomato pomace may be prepared as food products suitable for consumption by dogs. These food products may be of any consistency or moisture content; i.e., the compositions may be moist, semi-moist, or dry food products. "Moist" food products are generally those with a moisture content of from 60% to 90% or greater. "Dry" food products are generally those with a moisture content of from 3% to 11%, and are often manufactured in the form of small pieces or kibbles. "Semi-moist food products generally have a moisture content of from 25% to 35%. The food products may also include components of more than one consistency, for example, soft, chewy meat-like particles or pieces as well as kibble having an outer cereal component or coating and an inner "cream" component.

In some embodiments, the food products that comprise tomato pomace may be prepared in a canned or wet form using conventional food preparation processes known to those of ordinary skill in the art. Typically, ground animal proteinaceous tissues are mixed with the other ingredients, such as cereal grains, suitable carbohydrate sources, fats, oils, and balancing ingredients, including special purpose additives such as vitamin and mineral mixtures, inorganic salts, cellulose, beet pulp and the like, and water in an amount sufficient for processing. The ingredients are mixed in a vessel suitable for heating while blending the components. Heating the mixture is carried out using any suitable manner, for example, direct steam injection or using a vessel fitted with a heat exchanger. Following addition of all of the ingredients of the formulation, the mixture is heated to a temperature of from 50° F. to 212° F. Although temperatures outside this range can be used, they may be commercially-impractical without the use of other processing aids. When heated to the appropriate temperature, the material will typically be in the form of thick liquid, which is dispensed into cans. A lid is applied and the container is hermetically sealed. The sealed can is then placed in convention equipment designed for sterilization of the contents. Sterilization is usually accomplished by heating to temperatures of greater than 230° C. for an appropriate time depending on the temperature used, the nature of the composition, and related factors. The compositions and food products of the present invention can also be added to or combined with food compositions before, during, or after their preparation.

In some embodiments, the food products may be prepared in a dry form using convention processes known to those of ordinary skill in the art. Typically, dry ingredients, including dried animal protein, plant protein, grains and the like are ground and mixed together. Liquid or moist ingredients, including fats, oils water, animal protein, water, and the like are added combined with the dry materials. The specific formulation, order of addition, combination, and methods and equipment used to combine the various ingredients can be selected from those known in the art. For example, in certain embodiments, the resulting mixture is process into kibbles or similar dry pieces, which are formed using an extrusion process in which the mixture of dry and wet ingredients is subjected to mechanical work at high pressure and temperature, forced through small openings or apertures, and cut off into the kibbles, e.g., with a rotating knife. The resulting kibble can be dried and optionally coated with one or more topical coatings comprising, e.g., flavors, fats, oils, powdered ingredients, and the like. Kibbles may also be prepared from dough by baking, rather than extrusion, in which the dough is placed into a mold before dry-heat processing.

In preparing a composition, any ingredient generally may be incorporated into the composition during the processing of the formulation, e.g., during and/or after mixing of the other components of the composition. Distribution of these components into the composition can be accomplished by conventional means. In certain embodiments, ground animal and/or poultry proteinaceous tissues are mixed with other ingredients, including nutritional balancing agents, inorganic salts, and may further include cellulose, beet pulp, bulking agents and the like, along with sufficient water for processing.

In some embodiments, the compositions are formulated so as to be easier to chew. In specific embodiments, the compositions and food products are formulated to address specific nutritional differences between species and breeds of animals, as well as one of more of the attributes of the animal. For example, canine foods, for example, are typically formulated based upon the life stage, age, size, weight, body composition, and breed.

The compositions that comprise an effective amount of tomato pomace are formulated as a nutritionally complete diet to meet the needs of a mature adult canine. These nutritionally complete diets that include sufficient nutrients for maintenance of normal health of a healthy animal on the diet. Nutritionally complete and balanced pet food compositions, e.g. for companion canines, are familiar to one of skill in the art. For example, substances such as nutrients and ingredients suitable for nutritionally complete and balanced animal feed compositions, and recommended amounts thereof, may be found for example, in the Official Publication of the Association of American Feed Control Officials, Inc. (AAFCO), Atlanta, Ga. (2012).

In another embodiment, treats comprising an effective amount of tomato pomace can be prepared by, for example, an extrusion or baking process similar to those described below for dry food to provide an edible product. Treats include, for example, compositions that are given to an animal to entice the animal to eat during a non-meal time. Treats may be nutritional, wherein the composition comprises one or more nutrients, and may, for example, have a composition as described above for food. Non-nutritional treats encompass any other treats that are non-toxic. Compositions can be coated onto the treat, incorporated into the treat, or both.

In another embodiment, an animal toy is provided that is a chewable or consumable toy. Such toys are typically prepared by coating any existing toy with an effective amount of tomato pomace. Toys therefore include, for example, chewable toys. Contemplated toys for dogs include, for example, artificial bones. In certain embodiments, the composition of the invention can form a coating on the surface of the toy or on the surface of a component of the toy, or it can be incorporated partially or fully throughout the toy, or both. A wide range of suitable toys are currently marketed. See, e.g., U.S. Pat. No. 5,339,771 (and references disclosed in U.S. Pat. No. 5,339,771). See also, e.g., U.S. Pat. No. 5,419,283 (and references disclosed in U.S. Pat. No. 5,419,283). It should be recognized that this invention contemplates both partially consumable toys (e.g., toys comprising plastic components) and fully consumable toys (e.g., rawhides and various artificial bones). It should be further recognized that this invention contemplates toys for companion animals and particularly for use by a cat or a dog.

All publications mentioned herein are incorporated by reference for the purpose of describing and disclosing the materials and methodologies that are reported in the publication, which might be used in connection with the invention.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

EXAMPLES

Example 1

Blood is collected in order to determine plasma metabolomic profiles. Levels of 4-EPS in plasma can be measured by a commercial laboratory (Metabolon, Durham, N.C., USA). Extracted supernatant is split and run on gas chromatography and liquid chromatography mass spectrometer platforms. The peak for 4-EPS is known and the area under the peak for each sample can be normalized to a known sample. (See also: Evans, A. M., et al. (2009). Integrated, nontargeted ultrahigh performance liquid chromatography/ electrospray ionization tandem mass spectrometry platform for the identification and relative quantification of the small-molecule complement of biological systems. Anal. Chem. 81, 6656-6667.) Gas chromatography (for hydrophobic molecules) and liquid chromatography (for hydrophilic molecules) are used to identify and provide relative quantification of metabolites such as 4-EPS present in plasma samples. (See also: Ballet, C. et al. (2018) New enzymatic and mass spectrometric methodology for the selective investigation of gut microbiota-derived metabolites, Chem. Sci. 9, 6233-6239; Akiyama, Y et al. (2012) A Metabolomic Approach to Clarifying the Effect of AST-120 on 5/6 Nephrectomized Rats by Capillary Electrophoresis with Mass Spectrometry (CE-MS) Toxins 4(11):1309-1322; and Kikuchi K, et al. (2010) Metabolomic search for uremic toxins as indicators of the effect of an oral sorbent AST-120 by liquid chromatography/tandem mass spectrometry. J Chromatogr B Analyt Technol Biomed Life Sci 878:2997-3002.)

Example 2

Nucleotide-binding oligomerization domain 1, referred to as NOD1, is an intracellular sensor that detects small peptides derived from the cell wall component of intestinal microflora, which leads to innate immune responses. Innate immune responses through NOD1 activation plays a role in both in host defense against microbial infection and in the development of gastrointestinal disorders.

A genome wide association analysis (GWAS) which showed that there was a relationship between the SNP BICF2P1175095, which is located upstream of the NOD1 gene and circulating levels of 4-EPS. Dogs with CC genotype have an elevated risk of impaired gut colonization by certain beneficial microbes. This may lead to the growth of harmful microbes that may have effects on the distal organs such as the brain through certain microbial metabolites entering the systemic circulation. The known stress-related microbial metabolite, 4-EPS, is detected 9 times higher in dogs that have CC genotype.

Effective amounts of tomato pomace can reduce 4-EPS levels in dogs. Accordingly, tomato pomace will be specifically of benefit to those dogs with the CC genotype.

Example 3

A study was completed in which 40 dogs were randomly assigned into a control (20 dogs) or a test group (20 dogs) and received either a basal diet containing tomato pomace or a food without tomato pomace for 30 days. After a washout period of one month, a cross-over was performed to feed the groups the foods they did not previously receive. After 30 days, blood samples were collected to measure 4-ethylphenyl sulfate levels by metabolomics. Therefore, all dogs received either the food with or the food without tomato pomace for 30 days with metabolomics analysis completed at the end of each 30-day feeding period.

The results showed that dogs prone to having high 4-EPS may benefit from the consumption of food containing specific levels of tomato pomace. A matched-pair analysis comparing levels of 4-EPS in each dog after the consumption of the foods showed a significant reduction in 4-EPS due to the added tomato pomace (P=0.04) (FIG. 1).

Daily intakes of tomato pomace that lead to low levels of 4-EPS are indicated in Table 1. The lowest level of 4-EPS was achieved with an average daily intake of, on a dry matter basis, 0.14% tomato pomace, which is the equivalent of 0.24 grams tomato pomace per about 172 total grams per day. A daily consumption of, on a dry matter basis, 0.087% to 0.21% tomato pomace which is equivalent to 0.15 grams to 0.35 grams tomato pomace on a dry matter basis per about 172 total grams based on dry matter, per day led to low 4-EPS levels in the circulation.

TABLE 1

| Daily Tomato Pomace intake (grams) | Percent Daily Tomato Pomace intake | 4-ethylphenyl sulfate (4-EPS) levels |
| --- | --- | --- |
| 0.147 | 0.086982249 | 0.646914 |
| 0.1582 | 0.093609467 | 0.200801 |
| 0.1582 | 0.093609467 | 0.531001 |
| 0.1722 | 0.101893491 | 0.360281 |
| 0.1806 | 0.106863905 | 0.6152 |
| 0.182 | 0.107692308 | 0.435742 |
| 0.1974 | 0.116804734 | 0.382564 |
| 0.2058 | 0.121775148 | 0.669194 |
| 0.2086 | 0.123431953 | 0.356305 |
| 0.231 | 0.136686391 | 0.717677 |
| 0.2394 | 0.141656805 | 0.261394 |
| 0.2464 | 0.145798817 | 0.620934 |
| 0.2506 | 0.148284024 | 0.707654 |
| 0.252 | 0.149112426 | 0.334295 |
| 0.2604 | 0.15408284 | 0.665582 |
| 0.2632 | 0.155739645 | 0.730847 |
| 0.2674 | 0.158224852 | 0.616436 |
| 0.2814 | 0.166508876 | 0.505161 |
| 0.294 | 0.173964497 | 0.711769 |
| 0.2996 | 0.177278107 | 0.46275 |
| 0.3262 | 0.193017751 | 0.607899 |
| 0.3542 | 0.209585799 | 0.493352 |

When provided in an effective amount, tomato pomace reduces circulating levels of 4-EPS. Anti-stress food for pets can be formulated by inclusion of an effective amount of tomato pomace, thereby reducing blood levels of the microbial toxin, 4-EPS, which when increased is associated with stress, anxiety and brain damage. Such pet foods thereby address stress-related problems associated with elevated circulating levels of 4-EPS in pets.

Example 4

A saliva sample is obtained from a canine. The sample may be shipped as collected to a laboratory at another location, partially processed and then shipped to a laboratory at another location or completely processed and analyzed at a laboratory and the site of collection. If the sample is shipped as collected to a laboratory at another location or partially processed and then shipped to a laboratory at another location, results which may include some or all data collected from the sample by the laboratory may be transmitted to the site of collection and/or a veterinarian and/or the owner of or responsible party for the canine. After the saliva sample is obtained, it may be processed for analysis and evaluated for the presence of the CC genotype.

If results indicate that the canine is at an increased likelihood or risk of developing elevated 4-EPS levels, the canine may be administering compositions comprising an effective amount of tomato pomace.

Example 5

Samples are collected from canines using PERFORMAgene PG-100 Oral collection kit.

When doing so, the animal should not eat for 30 minutes or drink for 10 minutes before saliva collection, the individual doing the collection should not scrape the animal's teeth or cheek with the sponge nor should the animal be allowed to chew or bite the sponge.

The collection tube provided as part of the PERFORMAgene PG-100 Oral collection kit contains liquid that preserves the DNA sample and is required by the lab to analyze the sample. The cap should not be removed prior to sample collection.

In the first step of the collection protocol, the sponge is placed in the animal's mouth at the cheek pouch. Saliva is collected for 30 seconds by moving sponge and mopping saliva where it naturally pools (in the cheek pouch and under the tongue). For animals older than 6 months, moderate restraint may be required.

Next, holding the tube upright, the cap from the tube is unscrewed. The cap is turned upside down and the oral swab is placed in the tube. The cap is screwed on tightly to prevent liquid sample from leaking during transport. The tube is inverted and shaken vigorously numerous times, e.g. 10 times, to thoroughly mix sample.

A permanent marker may be used to clearly write the animal identification number on the white space available on the tube label.

The step-by-step laboratory protocol for manual purification of DNA from 0.5 mL aliquot of a Performagene™ sample that has been collected and preserved in Performagene chemistry with the PG-100 collection kit is as follows. The Reagents required for manual purification are available with PG-AC1 reagent package or PG-AC4 reagent package.

When a DNA sample is collected and mixed with the Performagene solution, the DNA is immediately stabilized Performagene samples are stable at room temperature for 1 year from the time of collection. Performagene samples can be stored indefinitely at −15° C. to −20° C., and can undergo multiple freeze-thaw cycles without deterioration of the DNA.

The following equipment and reagents are used in the purification process: a Microcentrifuge capable of running at 15,000×g; an air or water incubator at 50° C.; ethanol (95% to 100%) at room temperature; DNA buffer: TE (10 mM Tris-HCl, 1 mM EDTA, pH 8.0) or similar solution; optional glycogen (20 mg/mL) (e.g., Invitrogen Cat. No. 10814-010); ethanol (70%) at room temperature and 5M NaCl solution.

In the first step, the sample is mixed by shaking vigorously for 5 seconds. This is to ensure that viscous samples are properly mixed with the Performagene solution.

The sample is incubated in a 50° C. air incubator for a minimum of 2 hours, or in a 50° C. water incubator for a minimum of 1 hour. DNA in Performagene is stable at room temperature even without the incubation step. This heat-treatment step is essential to ensure that DNA is adequately released and that nucleases are permanently inactivated. This incubation step may be performed at any time after sample is collected from the animal and before it is purified. Incubation of the entire sample is recommended. The sample may be incubated at 50° C. overnight if it is more convenient. A longer time is required in an air incubator because temperature equilibration is slower than in a water incubator.

Optionally, the collection sponge may be removed. The cap is removed and the collection sponge is pressed against the inside of the tube to extract as much of the sample as possible. The sponge and cap are discarded. Sponge removal is dictated by preference of workflow.

Next, 500 µL of the mixed Performagene sample is transferred to a 1.5 mL microcentrifuge tube. The remainder of the Performagene sample can be stored at room temperature or frozen (−15° C. to −20° C.). 20 µL (1/25th volume) of PG-L2P purifier is then added to the microcentrifuge tube and mixed by vortexing for a few seconds. The sample becomes turbid as impurities and inhibitors are precipitated.

The sample is incubated on ice for 10 minutes (room temperature incubation can be substituted but will be slightly less effective in removing impurities) followed by centrifugation at room temperature for 5 minutes at 15,000×g. A longer period of centrifugation (up to 15 minutes) may be beneficial in reducing the turbidity (high A320) of the final DNA solution. The clear supernatant is transferred with a pipette tip into a fresh microcentrifuge tube and the pellet, which contains turbid impurities, is discarded. To 500 µL of supernatant, 25 µL (1/20$^{th}$ volume) of 5 M NaCl is added followed by mixing. The addition of NaCl is necessary to ensure efficient recovery of DNA. To 500 µL of supernatant, 600 µL of room temperature 95% to 100% ethanol is added followed by gentle mixing by inversion 10 times. During mixing with ethanol, the DNA will be precipitated. The DNA may appear as a clot of DNA fibers or as a fine precipitate, depending upon the amount of DNA in the sample. Even if no clot is seen, DNA will be recovered by carefully following the next steps.

The sample is allowed to stand at room temperature for 10 minutes to allow the DNA to fully precipitate. The tube is then placed in the centrifuge in a known orientation (DNA pellet may not be visible after centrifugation) and centrifuged at room temperature for 2 minutes at >15,000×g. For example, each tube may be placed in the microcentrifuge with the hinge portion of the cap pointing away from the center of the rotor. After centrifugation, the position of the pellet can be located (even if too small to be easily visible); it will be at the tip of the tube below the hinge.

The supernatant is removed with a pipette tip and discarded. The pellet contains DNA. Rotating the tube such that the pellet is on the upper wall will allow you to safely move a pipette tip along the lower wall and remove all of the supernatant. The supernatant may contain impurities and should be removed as completely as possible. Excessive drying of the pellet can make the DNA more difficult to dissolve. The DNA is washed by first adding 250 µL of 70% ethanol, then letting it stand for 1 minute at room temperature. The ethanol is removed with a pipette tip without disturbing the pellet. The 70% ethanol wash helps to remove residual inhibitors. Complete removal of ethanol, however, is essential to prevent inhibition during downstream applications. Therefore, the tube is centrifuged for 6 seconds to pool any remaining ethanol, which is removed with a pipette tip.

100 µL of DNA buffer (e.g. TE buffer) is added to the tube to dissolve the DNA pellet. Vortexing for at least 5 seconds aids in the dissolving process. To ensure complete rehydration of the DNA, let sit at room temperature overnight. DNA can now be quantified and used in downstream applications.

Assays that use fluorescent dyes are more specific than absorbance at 260 nm for quantifying the amount of double-stranded DNA (dsDNA) in a DNA sample. To quantify the DNA by fluorescence method, fluorescent dyes such as PicoGreen® or SYBR® Green I may be used to quantify dsDNA since there is less interference by contaminating RNA. Alternatively, commercially available kits such as Invitrogen's Quant-iT™ PicoGreen dsDNA Assay Kit (Cat. No. Q-33130) can be used. For either protocol, the purified DNA is preferably diluted 1:50 with TE solution and 5 µL is used in the quantification assay.

Alternatively, DNA may be quantified by absorbance in which case the purified sample is preferable first treated with RNase to digest contaminating RNA and then remove the RNA fragments by ethanol precipitation of the DNA. DNA from a Performagene sample typically contains appreciably more RNA than found in blood samples. Ensure that alcohol-precipitated DNA is fully dissolved before reading the absorbance. An absorbance of 1.0 at 260 nm corresponds to a concentration of 50 ng/µL (50 µg/mL) for pure dsDNA. A spectrophotometer cuvette capable of reading a volume of 100 µL or less should be used to avoid using too large a volume of sample. Absorbance values at 260 nm should be between 0.1 and 1.5. Lower values may not be reliable.

A 10 µL aliquot of purified RNase-treated DNA is diluted with 90 µL of TE (1/10 dilution) and mixed by gently pipetting up and down. Wait for bubbles to clear. TE is used in the reference (blank) cell. The absorbance is measured at 320 nm, 280 nm and 260 nm. Corrected $A_{280}$ and $A_{260}$ values are calculated by subtracting the absorbance at 320 nm ($A_{320}$) from $A_{280}$ and $A_{260}$ values. DNA concentration in ng/µL=corrected $A_{260}$×10 (dilution factor)×50 (conversion factor). $A_{260}/A_{280}$ ratio: divide corrected $A_{260}$ by corrected $A_{280}$.

Example 6

Genome-wide DNA Analysis using Illumina BeadChip technology and the Infinium HD assay can be used to detect CC genotype. Preferable the test is part of a panel that includes interrogation of one or more other clinically important SNPs.

Starting with a sample comprising purified genomic DNA (200-400 ng), the sample undergoes PCR-free whole genome amplification to produce fragment DNA that interrogated for SNPs. To identify the CC genotype an Illumina Canine HD panel and an additional 50,000-100,000 custom genetic markers (SNPs) (The Illumina Canine HD panel, Illumina, Inc. San Diego, Calif.) can be used. Such a system can be used to interrogate samples for the presence of the CC genotype or BeadArray technology may be customized to be limited to fewer SNPs for screening.

The Illumina BeadArray technology is based on small silica beads that self-assemble in microwells on planar silica slides. Each bead is covered with hundreds of thousands of copies of a specific oligonucleotide that act as a capture sequence in the Infinium assay. Once the beads have self-assembled, a proprietary decoding process maps the location of every bead, ensuring that each one is individually quality controlled. The result of this manufacturing process is that every BeadChip undergoes rigorous testing to assure the highest possible quality standards. The Infinium assay can be scaled to unlimited multiplexing without compromising data quality, unlike many alternative PCR-dependent assays. The simple streamlined workflow is common across all products, no matter how many SNPs are being interrogated. Likewise, the data acquisition process and analysis are the same. The Infinium assay protocol features single-tube sample preparation and whole genome amplification without PCR or ligation steps significantly reducing labor and sample handling errors. After hybridizing unlabeled DNA sample on the Beadchip, two-step allele detection provides high call rates and accuracy. Selectivity and specificity are accomplished in two-steps. Target hybridization to bead-bound 50-mer oligos provides high selectivity while enzymatical single-base extension also incorporates a labeled nucleotide for assay readout. The staining reagent is optimized to provide a higher signal, and more balanced intensities between red and green channels. These features contribute to accuracy, high call rates and copy number data with low noise. The Infinium assay produces two-color readouts (one color for each allele) for each SNP in a genotyping study. Intensity values for each two-color channels, A and B, convey information about the allelic ratio at a single genomic locus. Typical studies incorporate values for a large number of samples (hundreds to tens of thousands) to ensure significant statistical representation. When these values are appropriately normalized and plotted distinct patterns (or clusters) emerge, in which samples have identical genotypes at an assayed locus exhibit similar signal profiles (A and B values) and aggregate in clusters. For diploid organisms, bi-allelic loci are expected to exhibit three clusters (AA, AB and BB). Genotype calls are based upon information derived from standard cluster file, which provides statistical data from a representative sample set. This enables genotypes to be called by referencing assay single intensities against known data for a given locus. Since the call accuracy is tied to the quality of the cluster data, having efficient and robust clustering algorithm is essential for accurate genotyping. The Illumina Gebtrain2 algorithm accurately and efficiently identifies cluster patters of genotyping samples and reports summary.

Example 7

A daily diet that comprises tomato pomace provides significant benefits to dogs identified as having elevated levels of 4-EPS. In some embodiments, methods may comprise feeding a dog suspected of having elevated 4-EPS a daily diet that comprises an effective amount of tomato pomace. In some embodiments, methods may comprise feeding a dog identified as having elevated 4-EPS a daily diet that comprises an effective amount of tomato pomace.

In some embodiments, methods may comprise measuring 4-EPS in a canine to identify the canine as having elevated 4-EPS and feeding a dog a daily diet that comprises an effective amount of tomato pomace.

In some embodiments, methods may comprise measuring 4-EPS in a canine and comparing the measured 4-EPS level to a positive reference standard value to identify the canine as having elevated 4-EPS and feeding a dog a daily diet that comprises an effective amount of tomato pomace. The positive reference standard value corresponds to a 4-EPS deemed to be an elevated level for a dog of comparable size, weight, age, breed inter alia. If the measured value is equal to or greater than the positive reference standard value, the dog is identified as having elevated 4-EPS and is treated by feeding the dog a daily diet that comprises an effective amount of tomato pomace.

In some embodiments, methods may comprise measuring 4-EPS in a canine and comparing the measured 4-EPS level of the canine subject to the measured 4-EPS level of a positive control sample to identify the canine as having elevated 4-EPS and feeding a dog a daily diet that comprises an effective amount of tomato pomace. The positive control sample is a representative sample that has a concentration of 4-EPS deemed to be an elevated level for a dog of comparable size, weight, age, breed inter alia. If the measured 4-EPS level of the canine subject is equal to or greater than the measured 4-EPS level of the positive control sample, the dog is identified as having elevated 4-EPS and is treated by feeding the dog a daily diet that comprises an effective amount of tomato pomace.

In some embodiments, the dog may initially be identified as having or suspected as having anxiety, an anxiety disorder or displaying symptoms of anxiety or an anxiety disorder. The dog may then be tested to determine if it has elevated 4-EPS levels by one of the methods described herein. If the results indicate that the dog has elevated 4-EPS, it is treated by feeding it a daily diet that comprises an effective amount of tomato pomace.

In some embodiments, the dog may initially be identified as having or suspected as having stress, a stress disorder or displaying symptoms of stress or a stress disorder. The dog may then be tested to determine if it has elevated 4-EPS levels by one of the methods described herein. If the results indicate that the dog has elevated 4-EPS, it is treated by feeding it a daily diet that comprises an effective amount of tomato pomace.

Example 8

The following composition is based upon total nutrition to be provided per day.

In some embodiments based on the total weight of the composition on a dry matter basis, the amount of tomato pomace is equal to 0.087-0.5%. In some embodiments based on the total weight of the composition on a dry matter basis, the amount of tomato pomace is equal to 0.044% to about 0.42%. In some embodiments based on the total weight of the composition on a dry matter basis, the amount of tomato pomace is equal to 0.066% to about 0.315%. In some embodiments based on the total weight of the composition on a dry matter basis, the amount of tomato pomace is equal to 0.087-0.21%. In some embodiments based on the total weight of the composition on a dry matter basis, the amount of tomato pomace is equal to about 0.14%.

In certain embodiments, compositions may comprise chicken in an amount of 5%, 7.5%, 10%, 12.5%, 15%, 17.5%, 20%, 22.5% or 25% based on the total weight of the composition on a dry matter basis. In certain embodiments, compositions may comprise egg protein in an amount of 4%, 5%, 6%, 7%, 8%, 9%, 10%, 11%, 12%, 13%, 14% or 15% based on the total weight of the composition on a dry matter basis. In certain embodiments, compositions may comprise corn gluten meal in an amount of 6%, 7%, 8%, 9%, 10%, 11%, 12%, 13%, 14%, 15%, 16%, 17%, 18%, 19%, or 20% based on the total weight of the composition on a dry matter basis. In certain embodiments, compositions may comprise a vegetable source in an amount of 0.5%, 0.6%, 0.7%, 0.8%, 0.9%, 1.0%, 1.1%, 1.2%, 1.3%, 1.4%, 1.5%, 1.6%, 1.7%, 1.8%, or 1.9%, or 2.0% based on the total weight of the composition on a dry matter basis. In certain embodiments, compositions may comprise, in addition to tomato pomace, an additional fruit source in an amount of 0.1%, 0.2%, 0.3%, 0.4%, 0.5%, 0.6%, 0.7%, 0.8%, 0.9%, 1.0%, 1.1%, 1.2%, 1.3%, 1.4%, or 1.5% based on the total weight of the composition on a dry matter basis. In certain embodiments, compositions may comprise a carbohydrate selected from millet, brewers rice, oat groats, and combinations thereof in an amount of 5%, 10%, 15%, 20%, 25%, 30%, 35%, 40%, 45%, or 50% based on the total weight of the composition on a dry matter basis. In particular aspects of these embodiments, composition of the invention may comprise a dry weight of a carbohydrate source within a range defined by any two of these values as endpoints.

Example 9

Table 2 describes certain embodiments having proportion of the composition (% of dry weight of component composition)

TABLE 2

| | |
|---|---|
| Tomato pomace | from about 0.044% to about 0.42%, or from about 0.066% to about 0.315%, or from about 0.087% to about 0.21%, or from about 0.14% |
| Protein | from about 5% to about 70%, or from about 10% to about 70%, or from about 10% to about 60% |
| Carbohydrate (preferably a nitrogen-free or essentially nitrogen-free extract) | from about 0% to about 50%, or from about 5% to about 45% |
| Fat | from about 2% to about 50%, or from about 5% to about 50%, or from about 5% to about 40% |
| Dietary fiber | from about 0% to about 40%, or from about 1% to about 20%, or from about 1% to about 5.5% |
| Nutritional balancing agents (e.g., vitamins, and minerals) | from about 0% to about 15%, or from about 2% to about 8% |

A daily diet that comprises an effective amount of tomato pomace may provide benefit to dogs identified as having stress. In some embodiments, the methods comprise identifying a dog as having or suspected of having stress, a stress disorder or displaying symptoms of stress or a stress disorder and feeding it a daily diet that comprises an effective amount of tomato pomace.

Methods are provided that comprise feeding a dog a daily diet that comprises an amount of tomato pomace equal to 0.044% to 0.42% of nutritional intake per day. In some embodiments, the methods provided comprise feeding a dog a daily diet that comprises an amount of tomato pomace equal to 0.066% to 0.315% of nutritional intake per day. In some embodiments, the methods provided comprise feeding a dog a daily diet that comprises an amount of tomato pomace equal to 0.087% to 0.21% of nutritional intake per day. In some embodiments, the methods provided comprise feeding a dog a daily diet that comprises an amount of tomato pomace equal to about 0.14% of nutritional intake per day.

Example 10

Table 3 describes ingredients used in certain embodiments having proportion of the composition (% of dry matter weight of component composition).

TABLE 3

| Description | Content Range (w/w %) |
|---|---|
| Tomato pomace | 0.044 to 0.42, or 0.066 to 0.315, or 0.087 to 0.21, or 0.14 |
| Chicken, livers, hydrolyzed, dry | 25-45 |
| Hyvital ® wheat glutamine PN | 0.25-2 |
| Lysine, 1, hydrochloride | 0.1-0.75 |
| Methionine, dl | <0.08 |
| Taurine | 0.075-0.2 |
| Captex ® 355 Medium Chained Triglyceride | 1-5 |
| Cellulose, coarse | 1-5 |
| Beet, pulp | 1-3 |
| OatWell ® 22 oat bran | 2-5 |
| Pecan Fiber | 1-5 |
| MEG-3 ® 0355TG Fish Oil | 0.5-2.5 |
| Ginger Root Powder | 0.5-2 |
| Cranberry Pomace | 0.1-0.4 |
| Pomegranate Extract WS | 0.1-0.4 |
| Green Tea PE 50% EGCG WS | 0.1-0.4 |
| Boswellia PE 65% Boswellic Acids | 0.05-0.3 |
| Sensimune ™ 75 (Yeast Cell Wall) | 0.05-0.3 |

Example 11

Table 4 describes ingredients used in certain embodiments having proportion of the composition (% of dry matter weight of component composition).

TABLE 4

| Ingredient | w/w % |
|---|---|
| Tomato pomace | 0.044 to 0.42, or 0.066 to 0.315, or 0.087 to 0.21, or 0.14 |
| Chicken, livers, hydrolyzed, dry | 36.79 to 37.79 |
| Corn, starch, common canning | 32.45 to 32.45 |
| Choice White Grease | 1.00 |
| Mineral, premix, 2305 | 0.08 |
| Vitamin E, oil, 29% | 0.10 |
| Hyvital ® Wheat Glutamine PN | 1.00 |
| Lysine, 1, hydrochloride | 0.50 |
| Methionine, dl | 0.07 |
| Taurine | 0.10 |
| Captex ® 355 Medium Chained Triglyceride | 4.00 |
| Cellulose, coarse | 3.00 |
| Lactic acid, food grade | 1.50 |
| Dicalcium phosphate | 1.20 |
| Chicken, liver, digest, optimizor LDPE H | 2.00 |
| Sodium chloride, iodized | 0.40 |
| Choline chloride, liquid, 70% | 0.25 |
| Calcium carbonate | 2.00 |
| Potassium chloride | 0.70 |
| Beet, pulp | 2.50 |
| OatWell ® 22 oat bran | 3.00 |
| Pecan Fiber | 2.00 |
| MEG-3 ® 0355TG Fish Oil | 1.50 |
| Ginger Root Powder | 1.00 |
| Palatant | 0.75 |
| Natural flavor, Pork, Liver, Digest, D'T | 0.50 |
| Glyceryl monostearate | 0.25 |
| Cranberry Pomace | 0.20 |

TABLE 4-continued

| Ingredient | w/w % |
|---|---|
| Pomegranate Extract WS | 0.20 |
| Green Tea PE 50% EGCG WS | 0.20 |
| Boswellia PE 65% Boswellic Acids | 0.20 |
| Sensimune ™ 75 (Yeast Cell Wall) | 0.15 |

Example 12

Table 5 describes ingredients used in certain embodiments having proportion of the composition (% of dry matter weight of component composition).

TABLE 5

| Ingredient | w/w % |
|---|---|
| Tomato pomace | 0.044 to 0.42, or 0.066 to 0.315, or 0.087 to 0.21, or 0.14 |
| Rice, brewers | 25.00 to 26.00 |
| Pea, protein concentrate | 10.00 to 11.00 |
| Chicken Dried 10% Ash | 8.00 to 9.00 |
| Chicken, ground, fresh | 7.00 to 8.00 |
| Sorghum, whole | 6.36 |
| Chicken Meal | 6.14 |
| Pork Fat, Choice White Grease | 1.00 |
| Flax, seed, whole | 3.00 |
| Eggs, dried, granulated | 5.50 |
| Pecan Fiber | 4.80 |
| G03 Buckwheat Groats | 4.00 |
| Oat, groats | 4.00 |
| Captex 355 Medium Chained Triglyceride | 3.00 |
| Chicken, liver, digest, optimizor LDPE H | 2.00 |
| Oat, fiber | 1.50 |
| Beet, pulp, ground, fine | 1.50 |
| Lactic acid, food grade | 1.50 |
| Fish oil, TG, 18/12, NP | 1.20 |
| Flav Gen#1 + CWG | 1.00 |
| Potassium chloride | 0.30 |
| Carnitine, 1, 10% | 0.27 |
| Natural flavor, Pork, Liver, Digest, D'T | 0.25 |
| Choline chloride, liquid, 70% | 0.18 |
| Sensimune 75 (Yeast Cell Wall) | 0.15 |
| Vitamin E, oil, 29% | 0.14 |
| Taurine | 0.10 |
| Sodium chloride, iodized | 0.10 |
| Lysine, 1, hydrochloride | 0.10 |
| Mineral, premix, 2305 | 0.04 |
| Oat Fiber, Fruit, Vegetable blend | 0.04 |
| Dicalcium phosphate | 0.04 |

Example 13

Table 6 describes ingredients used in certain embodiments having proportion of the composition (% of dry matter weight of component composition).

TABLE 6

| Ingredient | w/w % |
|---|---|
| Tomato pomace | 0.044 to 0.42, or 0.066 to 0.315, or 0.087 to 0.21, or 0.14 |
| Rice, Brewers | — |
| Chicken Meal | 7.00 to 8.00 |
| Pea, protein concentrate | 8.00 to 9.00 |
| Cellulose, coarse | 4.00 to 5.00 |
| Chicken Dried 10% Ash | 6.00 to 7.00 |
| Barley, pearled, cracked | 20.00 to 21.00 |
| Chicken, ground, fresh | 8.00 to 9.00 |
| Flax, seed, whole | 2.00 |
| Coconut oil preserved | 4.00 |
| Chicken, liver, digest, optimizor LDPE H | 3.00 |
| Lactic acid | 1.50 |
| Methionine, dl | 0.64 |
| Potassium chloride | 0.50 |
| Sodium chloride, iodized | 0.60 |
| Fish oil, TG, 18/12, NP | 0.50 |
| Calcium carbonate | 0.30 |
| Choline chloride, liquid, 70% | 0.25 |
| Carnitine, 1, 10% | 0.30 |
| Vitamin E, oil, 29% | 0.17 |
| Mineral, premix, 2305 | 0.08 |
| Taurine | 0.06 |
| Oat, groats | 10.00 |
| Buckwheat Groats | 6.92 |
| Pea, bran, meal | 5.00 |
| Tomato, pomace, | 5.00 |
| Beet, pulp, ground, fine | 3.00 |

Example 14

Table 7 describes ingredients used in certain embodiments having proportion of the composition (% of dry matter weight of component composition).

TABLE 7

| Ingredient | w/w % | w/w % |
|---|---|---|
| Tomato pomace | 0.044 to 0.42, or 0.066 to 0.315, or 0.087 to 0.21, or 0.14 | 0.044 to 0.42, or 0.066 to 0.315, or 0.087 to 0.21, or 0.14 |
| Corn starch | 31.10 | 48.11 |
| Hydrolyzed chicken liver and heart | 37.00 | 32.00 |
| Soybean oil, crude, degummed | 3.60 | 4.66 |
| Cellulose, pelleted | — | 3.94 |
| Chicken, liver, digest, optimizer LDPE H | 2.00 | 2.00 |
| Lactic acid, food grade | 1.50 | 1.50 |
| Calcium carbonate | 1.22 | 1.22 |
| Dicalcium phosphate | 1.22 | 1.22 |
| Choice White Grease/Phos Acid | 1.25 | 1.00 |
| Flav Gen#1 + CWG | 1.25 | 0.75 |
| Glyceryl monostearate | 0.74 | 0.74 |
| Potassium chloride | 0.69 | 0.69 |
| Natural flavor, Pork, Liver, Digest, D'T | 0.75 | 0.50 |
| Sodium chloride, iodized | 0.44 | 0.44 |

TABLE 7-continued

| Ingredient | w/w % | w/w % |
|---|---|---|
| Choline chloride, liquid, 70% | 0.38 | 0.38 |
| Methionine, dl | 0.30 | 0.30 |
| Sodium tripolyphosphate | 0.15 | 0.15 |
| Vitamin premix | 0.12 | 0.12 |
| Mineral, premix, 2305 | 0.07 | 0.07 |
| Taurine | 0.02 | 0.02 |
| Pecan shells, ground | 7.00 | — |
| Flax seed whole brown | 3.00 | — |
| Beet pulp, ground, fine | 2.50 | — |
| Cranberry pomace | 1.00 | — |

Example 15

Table 8 describes ingredients used in certain embodiments having proportion of the composition (% of dry matter weight of component composition).

TABLE 8

| Ingredient | w/w % | w/w % |
|---|---|---|
| Tomato pomace | 0.044 to 0.42, or 0.066 to 0.315, or 0.087 to 0.21, or 0.14 | 0.044 to 0.42, or 0.066 to 0.315, or 0.087 to 0.21, or 0.14 |
| Chicken meal | 15.36 | 15.36 |
| Rice, brewers | 8.64 | 8.64 |
| Eggs, dried, granulated | 8.00 | 8.00 |
| Corn, gluten, meal | 7.62 | 7.62 |
| Sorghum, whole | 5.00 | 5.00 |
| Choice white grease/Phos Acid | 4.00 | 4.00 |
| Palatant, 12 L, Liquid | 3.00 | 3.00 |
| Lactic acid, food grade | 1.50 | 1.50 |
| Soybean oil, crude, degummed | 1.05 | 1.05 |
| Palatant, ITE2, Dry | 1.00 | 1.00 |
| Potassium chloride | 0.89 | 0.89 |
| Sodium chloride, iodized | 0.61 | 0.61 |
| Calcium carbonate | 0.41 | 0.41 |
| Dicalcium phosphate | 0.25 | 0.25 |
| Vitamin E, oil, 29% | 0.17 | 0.17 |
| Choline chloride, liquid, 70% | 0.16 | 0.16 |
| Mineral, premix, 2305 | 0.06 | 0.06 |
| Tryptophan | 0.04 | 0.04 |
| Taurine | 0.04 | 0.04 |
| Cellulose, pelleted | — | 1.50 |
| Corn, yellow, whole | 26.00 | 40.00 |
| Pecan shells, ground | 7.00 | — |
| Flax seed whole brown | 3.00 | — |
| Beet pulp, ground, fine | 2.50 | 0.50 |
| Cranberry pomace | 1.00 | — |

Example 16

Table 9 describes ingredients used in certain embodiments having proportion of the composition (% of dry matter weight of component composition).

TABLE 9

| Ingredient | w/w % | w/w % | w/w % | w/w % | w/w % |
|---|---|---|---|---|---|
| Tomato pomace | 0.044-0.42, or 0.066-0.315, or 0.087-0.21, or 0.14 | 0.044-0.42, or 0.066-0.315, or 0.087-0.21, or 0.14 | 0.044-0.42, or 0.066-0.315, or 0.087-0.21, or 0.14 | 0.044-0.42, or 0.066-0.315, or 0.087-0.21, or 0.14 | 0.044-0.42, or 0.066-0.315, or 0.087-0.21, or 0.14 |
| Coconut Oil | up to 14.2 | up to 7.1 | up to 14.2 | up to 13.0 | up to 13.0 |
| Protein | up to 19.7 | up to 24.7 | up to 24.7 | up to 24.8 | up to 24.8 |
| Fat | up to 20.6 | up to 16.9 | up to 16.9 | up to 22.0 | up to 22.0 |
| Carbohydrate | up to 53.8 | up to 51.0 | up to 51.0 | up to 46.3 | up to 27.6 |
| Crude Fiber | up to 0.37 | up to 2.6 | up to 2.6 | up to 1.4 | up to 21.0 |

The invention claimed is:

1. A method of reducing levels of 4-ethylpheynyl sulfate in a canine subject, comprising:
   identifying a canine subject as being at an increased likelihood of developing elevated levels of 4-ethylpheny] sulfate, comprising:
   analyzing a biological sample obtained from the canine subject for the presence of two copies of the minor allele C of the single nucleotide polymorphism BICF2P1175095 in the canine subject;
   detecting the presence of the two copies of the minor allele of the single nucleotide
   polymorphism BICF2P1175095, wherein the presence of the two copies of the minor allele of BICF2P1175095 indicates that the canine subject has an increased likelihood of developing elevated levels of 4-ethylpheny] sulfate within its lifetime; and
   administering to the canine subject an effective amount of a food composition comprising tomato pomace equal to 0.087% to 0.21% of nutritional intake per day.

2. The method of claim 1 wherein the sample is analyzed by performing DNA sequencing, restriction enzyme digest, polymerase chain reaction (PCR), hybridization, real-time PCR, reverse transcriptase PCR, or ligase chain reaction.

3. The method of claim 1, wherein the sample is a genomic DNA sample.

4. The method of claim 1, wherein the sample is obtained from blood, saliva, follicle root, nasal swab or oral swab of the canine subject.

5. The method of claim 1, wherein the sample is analyzed by performing at least one nucleic acid analysis technique selected from: DNA sequencing, restriction enzyme digest, polymerase chain reaction (PCR), hybridization, real-time PCR, reverse transcriptase PCR, or ligase chain reaction.

6. The method of claim 1, wherein the sample is analyzed by performing at least one nucleic acid analysis technique selected from: analysis using a whole genome SNP chip, single-stranded conformational polymorphism (SSCP) assay, restriction fragment length polymorphism (RFLP), automated fluorescent sequencing; clamped denaturing gel electrophoresis (CDGE); denaturing gradient gel electrophoresis (DGGE), mobility shift analysis, restriction enzyme analysis, heteroduplex analysis, chemical mismatch cleavage (CMC), RNase protection assays, use of polypeptides that recognize nucleotide mismatches, allele-specific PCR, sequence analysis, and SNP genotyping.

7. The method of claim 1, wherein the sample is analyzed by performing at least one nucleic acid analysis technique selected from: hybridization-based methods, enzyme-based methods, post-amplification methods based on physical properties of DNA, and sequencing methods.

8. The method of claim 1, wherein the sample is analyzed by performing at least one nucleic acid analysis technique selected from: hybridization-based methods selected from the group consisting of dynamic allele-specific hybridization, molecular beacon methods and SNP microarrays; enzyme-based methods selected from the group consisting of restriction fragment length polymorphism (RFLP), PCR-based methods, Flap endonuclease, primer extension methods, 5'-nuclease and oligonucleotide ligation assay; post-amplification methods based on physical properties of DNA selected from the group consisting of single strand conformation polymorphism, temperature gradient gel electrophoresis, denaturing high performance liquid chromatography, high-resolution amplicon melting, DNA mismatch-binding proteins, SNPlex, and surveyor nuclease assay; and sequencing methods.

9. The method of claim 1 wherein the canine subject exhibits symptoms of canine anxiety or canine stress prior to analyzing the biological sample.

10. The method of claim 1, wherein the canine subject is fed the food composition in an amount sufficient to provide the canine subject tomato pomace equal to about 0.14% of nutritional intake per day.

11. The method of claim 1, wherein the canine has previously been identified as having canine anxiety.

12. The method of claim 1, wherein the canine has previously been identified as having canine stress symptoms.

* * * * *